United States Patent
Beke et al.

(10) Patent No.: US 8,034,827 B2
(45) Date of Patent: Oct. 11, 2011

(54) PHENANTHRIDINE DERIVATIVES AS BRADYKININ ANTAGONISTS

(75) Inventors: Gyula Beke, Budakeszi (HU); Eva Bozo, Budapest (HU); Gabor Czira, Budapest (HU); Janos Eles, Budapest (HU); Sandor Farkas, Budapest (HU); Katalin Hornok, Budapest (HU); Eva Schmidt, Budapest (HU); Eva Szentirmay, Erd (HU); Istvan Vago, Budapest (HU); Monika Vastag, Budapest (HU)

(73) Assignee: Richter Gegeon Nyrt., Budapest (HU)

( * ) Notice: Subject to any disclaimer, the term of this patent is extended or adjusted under 35 U.S.C. 154(b) by 496 days.

(21) Appl. No.: 12/158,606

(22) PCT Filed: Dec. 19, 2006

(86) PCT No.: PCT/HU2006/000120
§ 371 (c)(1),
(2), (4) Date: Nov. 10, 2008

(87) PCT Pub. No.: WO2007/072092
PCT Pub. Date: Jun. 28, 2007

(65) Prior Publication Data
US 2009/0270411 A1    Oct. 29, 2009

(30) Foreign Application Priority Data
Dec. 20, 2005 (HU) .................... 0501169

(51) Int. Cl.
*A61K 31/44* (2006.01)
*C07D 211/68* (2006.01)
(52) U.S. Cl. ................... 514/298; 546/285; 544/359
(58) Field of Classification Search .................. 514/298; 546/285; 544/359
See application file for complete search history.

(56) References Cited

U.S. PATENT DOCUMENTS
4,529,728 A    7/1985  Fabre et al.
7,056,937 B2 *  6/2006  Grant et al. .................. 514/353

FOREIGN PATENT DOCUMENTS
| WO | WO 00/75107 | 12/2000 |
| WO | WO 02/76964 | 10/2002 |
| WO | WO 02/99388 | 12/2002 |
| WO | WO 04/54584 | 7/2004 |
| WO | WO 05/04810 | 1/2005 |

OTHER PUBLICATIONS

Miura et al., 1998, CAS: 129: 175521.*
Bergbreiter et al., "Soluble polymer-supported catalysts containing azo dyes,"*Org. Lett.*, 2002, 4(5):737-740.
Ferreira et al., "Evidence for the participation of kinins in Freund's adjuvant-induced inflammatory and nociceptive responses in kinin B1 and B2 receptor knockout mice," *Neuropharmacol.*, 2001, 41(8):1006-1012.

Hess et al., "Cloning and pharmacological characterization of a human bradykinin (BK-2) receptor," *Biochem. Biophys. Res. Commun.*, 1992, 184:260-268.
Leeb-Lundberg et al., "International Union of Pharmacology. XLV. Classification of the Kinin Receptor Family: from Molecular Mechanisms to Pathophysiological Consequences," *Pharmacol. Rev.*, 2005, 57:27-77.
Ma et al., "Basal expression of bradykinin B(1) receptor in the spinal cord in humans and rats," *Neuroreport*, 2001, 12(11):2311-2314.
Ma et al., "Basal expression of bradykinin B1 receptor in peripheral sensory ganglia in the rat," *Neuroreport*, 2000, 11(18):4003-4005.
Ma, "The expression of bradykinin B1 receptors on primary sensory neurones that give rise to small caliber sciatic nerve fibres in rats," *Neuroscience*, 2001, 107(4):665-673.
Marceau, "A possible common pharmacophore in the non-peptide antagonists of the bradykinin B1 receptor," *Trends in Pharmacological Sciences*, 2005, 26(3):116-118.
Menke et al., "Expression cloning of a human B1 bradykinin receptor," *J. Biol. Chem.*, 1994, 269(34):21583-21586.
Miura et al., "Oxidative Cross-Coupling of N-(2'-Phenylphenyl)benzene- sulfonamides or Benzoic and Naphthoic Acids with Alkenes Using a Palladium-Copper Catalyst System under Air, " *J. Org. Chem.*, 1998, 63(15):5211-5215.
Pesquero et al., "Hypoalgesia and altered inflammatory responses in mice lacking kinin B1 receptors," *PNAS*, 2000, 97(14):8140-8145.
Ransom et al., "Pharmacological characterization and radioligand binding properties of a high-affinity, nonpeptide, bradykinin B1 receptor antagonist," *Eur. J. Pharmacol.*, 2004, 499:77-84.
Stemp et al., "Design and synthesis of trans-N-[4-{2-(6-cyano-1,2,3,4-tetrahydroisoquinolin-2-yl)ethyl}-4-quinolinecarboxamide {SB-277011}: a potent and selective dopamine D3 receptor antagonist with high oral bioavailability and CNS penetration in the rat," *J. Med. Chem.*, 2000, 43:1878-1885.

(Continued)

Primary Examiner — Rei-tsang Shiao
(74) Attorney, Agent, or Firm — Fish & Richardson P.C.

(57) ABSTRACT

The present invention relates to new phenanthridine derivatives of formula (I), wherein the variables are as defined in the specification, to processes for producing the same, to pharmacological compositions containing the same and to their use in therapy or prevention of painful and inflammatory processes.

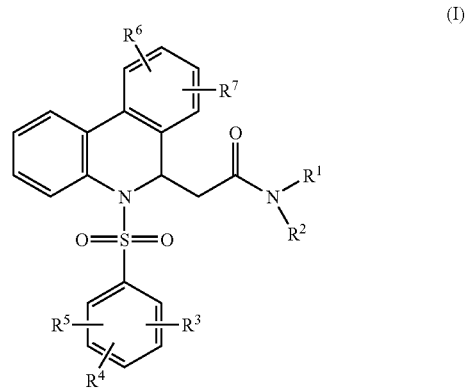

(I)

7 Claims, No Drawings

OTHER PUBLICATIONS

Su et al., "Discovery of a Potent, Non-peptide Bradykinin B1 Receptor Antagonist," *J. Am. Chem. Soc.*, 2003, 125(25):7516-7517.

Uhlmann and Pfleiderer, "Substituted β-Phenyl-ethyl Groups. New Blocking Groups for Oligonucleotide Syntheses by the Phosphotriester Approach," *Helvetica Chimica Acta*, 1981, 64(5):1688-1703.

Wood et al., "Benzodiazepines as Potent and Selective Bradykinin B1 Antagonists," *J. Med. Chem.*, 2003, 46(10):1803-1806.

Wotherspoon and Winter, "Bradykinin B1 receptor is constitutively expressed in the rat sensory nervous system," *Neuroscience Letters*, 2000, 294(3):175-178.

\* cited by examiner

PHENANTHRIDINE DERIVATIVES AS BRADYKININ ANTAGONISTS

CROSS-REFERENCE TO RELATED APPLICATIONS

This application is a National Stage application under 35 U.S.C. §371 and claims benefit under 35 U.S.C. §119(a) of International Application No. PCT/HU20006/000120 having an International Filing Date of Dec. 19, 2006, which claims the benefit of priority of HU P05 01169 having a filing date of Dec. 20, 2005. The contents of each of the prior applications are hereby incorporated by reference in their entirety.

1. Field of the Invention

The present invention relates to new phenathridine derivatives of formula (I) and optical antipodes or racemates and/or salts and/or hydrates and/or solvates thereof which are useful in the treatment or prevention of painful and inflammatory processes. The present invention also relates to the processes for producing compounds of formula (I) and to pharmacological compositions containing the same.

BACKGROUND OF THE INVENTION

Kinins are endogenous peptides formed in plasma and peripheral tissues in response to tissue injury or infection following catalytic cleavage of kininogens by kallikrein enzymes. Kinins play an important role in the pathophysiological processes accompanying pain and inflammation. Their biological actions are mediated by two G-protein coupled membrane receptors, denoted B1 and B2. Both B1 and B2 receptors have been cloned [*Biochem. Biophys. Res. Commun.*, 184 (1992) 260-268 and *J. Biol. Chem.*, 269 (1994) 21583-21586] and the mechanisms regulating their expression, self-maintenance and signaling function is under intensive investigations [*Pharmacol. Rev.*, 57 (2005) 27-77].

The first set of kinins, bradykinin (BK) and kallidin (LysBK) preferentially act through stimulation of constitutively expressed and rapidly desensitizing B2 receptors, which are widely distributed in many tissues. On the other hand, their active carboxypeptidase metabolites, the second set of kinins, desArg$^9$BK (DABK) and LysdesArg$^9$BK (LysDABK) activate inducible and non-desensitising B1 receptors, which are rarely expressed under non-pathological conditions. Generally B1 receptors rapidly appear after injuries of various natures (tissue trauma, infections, etc.). Thus the B1 receptor up-regulation appears to be part of a generalized response that includes the local co-expression (eventually up-regulation) of enzymes, receptors, autacoids, cytokines and chemokines that notoriously play key roles in the early and late responses of tissues to various types of injury.

In animal models it has been demonstrated that there is a switch in dominance of function from B2 to B1 in chronic inflammatory states. While the B2 receptor is implicated in the acute phase of the inflammatory and pain response, the B1 receptor is involved in the chronic phase of this response. The involvement of kinin receptors in inflammation and pain transduction has been supported by the results of studies on mice lacking bradykinin B1 receptors. B1 receptor deficient mice are different from wild-type mice in sensory functions, exhibiting increased analgesic thresholds to noxious chemical and heat stimuli, and drastic reduction in the accumulation of polymorphonuclear leukocytes at sites of inflammation [*PNAS*, 97 (2000) 8140-8145 and *Neuropharmacology* 41 (2201) 1006-1012]. Furthermore the most original, finding in B1 receptor deficient mice was the direct evidence for a role of central kinin receptors in nociception suggesting that the hypoalgesia seen in B1-receptor knockout mice is partly due to reduced central sensitisation in the spinal cord. However, apart from the above changes B1 knockout mice were apparently normal without any apparent pathological changes.

Apart from the evidence of basal expression of B1 receptors on the periphery recently more and more evidence shows that B1 receptors are constitutively expressed 'centrally' in some neuronal elements, including the spinal cord and some higher structures as well. The function of these receptors is unclear but they have been implicated in pain transmission and hyperalgesia. Therefore, B1 receptor antagonists are believed to be useful in alleviating pain not only via peripheral sites but also to have possibly broader spectrum of analgesic effects if they block central B1 receptors as well [*NeuroReport* 11 (2000) 4003-4005; *NeuroReport*, 12 (2001) 2311-2313; *Neuroscience* 107 (2001) 665-673 and *Neuroscience Letters* 294 (2000) 175-178].

On the basis of scientific data bradykinin receptors are involved in mediation of pain and hyperalgesia in several ways. B1 receptor antagonists may have diverse modes of action. They have (1) indirect ('peripheral') effects on the nociceptors via inhibition of release of other algogenic mediators (prostaglandins, cytokines and nitric oxide) from cells other than sensory neurones (macrophages, fibroblasts or endothelial cells); (2) direct ('peripheral') effects on nociceptors expressing B1 receptors (constitutively) or upon induction and (3) 'central' effects on pain processing in the superficial dorsal horn of spinal cord.

Therefore, an orally active non-peptide bradykinin B1 receptor antagonist could be a potential therapeutic agent in the treatment of chronic inflammatory pain.

SUMMARY OF THE INVENTION

We have found a class of phenathridine derivatives which have high affinity for bradykinin B1 receptors and selectivity over bradykinin B2 receptors. The selectivity is particularly important as the undesired side effects of the compounds are much less pronounced.

The present invention relates to new phenathridine derivatives of formula (I)

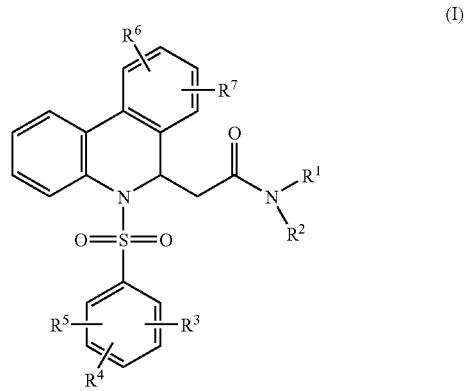

wherein
$R^1$ is hydrogen atom or $C_1$-$C_4$ alkyl group;
$R^1$ is selected from (1) hydrogen atom; with the proviso that $R^1$ and $R^2$ can not be simultaneously hydrogen atom; (2) —(CH$_2$)$_n$—NR$^a$R$^b$, (3) —(CH$_2$)$_n$—CO—NR$^a$R$^b$, (4) —(CH$_2$)$_m$—X-Q, (5) —CHR$^c$—NR$^a$R$^b$; or
$R^1$ and $R^2$ together with the nitrogen atom to which they are attached form a 4-7 membered heterocyclic ring containing 1-3 heteroatom selected from O, S and N; wherein said ring is optionally substituted with —CO—NR$^a$R$^b$, $C_1$-$C_4$ alkyl, 4-(4,5-dihydro-1H-imidazol-2-yl)-benzyl or 4-(1,4,5,6-tetrahydro-pyrimidin-2-yl)-benzyl;

R$^3$, R$^4$, R$^5$, R$^6$ and R$^7$ are independently of each other hydrogen atom, halogen atom, trifluoromethyl, $C_1$-$C_4$ alkyl, $C_1$-$C_4$ alkoxy, or acetyl group;

n is an integer from 1 to 4;

R$^a$ and R$^b$ are hydrogen atom, optionally substituted $C_1$-$C_4$ alkyl group, or R$^a$, R$^b$ and the nitrogen atom to which they are both attached together form a saturated, partially unsaturated or aromatic 4-7 membered ring containing 1-3 heteroatom selected from O, S and N; wherein said ring is optionally substituted with 1-piperidinyl, 2-piperidinyl, 4-piperidinyl, 2-pyridyl or 4-pyridyl group;

R$^c$ is methyl, hydroxymethyl, benzyl or phenyl group;

m is an integer from 0 to 6;

X is a single bond, O or S;

Q is a phenyl group, optionally substituted with [1,4']bipiperidinyl-1'-yl, 4,5-dihydro-1H-imidazol-2-yl, —(CH$_2$)$_n$—NH—(C=NH)—NH$_2$ or —(CH$_2$)$_m$—(C=NH)—NH$_2$ group; or 4-piperidinyl group, optionally substituted with 4-piperidinyl group; or $C_5$-$C_7$ cycloalkyl group, optionally substituted with —(CH$_2$)$_m$—NR$^a$R$^b$ group, and optical antipodes or racemates and/or salts and/or hydrates and/or solvates thereof.

The invention also relates to the pharmaceutical compositions containing the compounds of formula (I) or optical antipodes or racemates or salts or hydrates or solvates thereof as active ingredient.

Furthermore objects of the present invention are the synthesis of compounds of formula (I), and the chemical and pharmaceutical manufacture of medicaments containing these compounds, as well as the methods of treatment with these compounds, which means administering to a mammal to be treated—including human—effective amount/amounts of compounds of formula (I) of the present invention as such or as medicament.

DETAILED DESCRIPTION OF THE INVENTION

The present invention relates to new bradykinin B1 receptor antagonist phenathridine derivatives of formula (I)

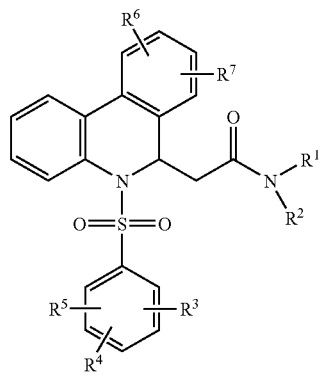

(I)

wherein

R$^1$ is hydrogen atom or $C_1$-$C_4$ alkyl group;

R$^2$ is selected from (1) hydrogen atom; with the proviso that R$^1$ and R$^2$ can not be simultaneously hydrogen atom; (2) —(CH$_2$)$_n$—NR$^a$R$^b$, (3) —(CH$_2$)$_n$—CO—NR$^a$R$^b$, (4) —(CH$_2$)$_m$—X-Q, (5) —CHR$^c$—NR$^a$R$^b$; or R$^1$ and R$^2$ together with the nitrogen atom to which they are attached form a 4-7 membered heterocyclic ring containing 1-3 heteroatom selected from O, S and N; wherein said ring is optionally substituted with —CO—NR$^a$R$^b$, $C_1$-$C_4$ alkyl, 4-(4,5-dihydro-1H-imidazol-2-yl)-benzyl or 4-(1,4,5,6-tetrahydro-pyrimidin-2-yl)-benzyl;

R$^3$, R$^4$, R$^5$, R$^6$ and R$^7$ are independently of each other hydrogen atom, halogen atom, trifluoromethyl, $C_1$-$C_4$ alkyl, $C_1$-$C_4$ alkoxy, or acetyl group;

n 0 is an integer from 1 to 4;

R$^a$ and R$^b$ are hydrogen atom, optionally substituted $C_1$-$C_4$ alkyl group, or R$^a$, R$^b$ and the nitrogen atom to which they are both attached together form a saturated, partially unsaturated or aromatic 4-7 membered ring containing 1-3 heteroatom selected from O, S and N; wherein said ring is optionally substituted with 1-piperidinyl, 2-piperidinyl, 4-piperidinyl, 2-pyridyl or 4-pyridyl group;

R$^c$ is methyl, hydroxymethyl, benzyl or phenyl group;

m is an integer from 0 to 6;

X is a single bond, O or S;

Q is a phenyl group, optionally substituted with [1,4']bipiperidinyl-1'-yl, 4,5-dihydro-1H-imidazol-2-yl, —(CH$_2$)$_n$—NH—(C=NH)—NH$_2$ or —(CH$_2$)$_m$—(C=NH)—NH$_2$ group; or 4-piperidinyl group, optionally substituted with 4-piperidinyl group; or $C_5$-$C_7$ cycloalkyl group, optionally substituted with —(CH$_2$)$_m$—NR$^a$R$^b$ group, and optical antipodes or racemates and/or salts and/or hydrates and/or solvates thereof.

The invention also relates to the pharmaceutical compositions containing the compounds of formula (I) or optical antipodes or racemates or salts or hydrates or solvates thereof as active ingredient.

Furthermore objects of the present invention are the synthesis of compounds of formula (I), and the chemical and pharmaceutical manufacture of medicaments containing these compounds, as well as the methods of treatment with these compounds, which means administering to a mammal to be treated—including human—effective amount/amounts of compounds of formula (I) of the present invention as such or as medicament.

The term "halogen" substituent denotes fluorine, chlorine, bromine or iodine atoms. The term $C_1$-$C_4$ alkyl group used in the present description denotes methyl, ethyl, normal- and isopropyl and different butyl groups. These $C_1$-$C_4$ alkyl groups can be in the $C_1$-$C_4$ alkoxy groups and $C_1$-$C_4$ alkoxycarbonyl groups.

The 4-7 membered heterocyclic ring in the meaning of R$^1$ and R$^2$ can be e.g. piperidine, pyrrolidine, piperazine, homopiperazine, morpholine, thiomorpholine and the like.

The $C_1$-$C_4$ alkyl group in the meaning of R$^a$ and R$^b$ can be substituted e.g. with 4-piperidinyl, 1-pyrrolidinyl or piperazinyl group.

The saturated, partially unsaturated or aromatic 4-7 membered ring in the meaning of R$^a$ and R$^b$ can be e.g. piperidine, pyrrolidine, piperazine, homopiperazine, morpholine, thiomorpholine and the like.

The invention relates also to the salts of compounds of formula (I) formed with acids or bases.

Both organic and inorganic acids can be used for the formation of acid addition salts. Suitable inorganic acids can be e.g. hydrochloric acid, sulfuric acid and phosphoric acid. Representatives of monovalent organic acids can be e.g. formic acid, acetic acid, trifluoroacetic acid, propionic acid, and different butyric acids, valeric acids and capric acids. Representatives of bivalent organic acids can be e.g. oxalic acid, malonic acid, maleic acid, fumaric acid and succinic acid. Other organic acids can also be used, such as hydroxy acids e.g. citric acid, tartaric acid, or aromatic carboxylic acids e.g. benzoic acid or salicylic acid, as well as aliphatic and aromatic sulfonic acids e.g. methanesulfonic acid and p-toluenesulfonic acid. Especially valuable group of the acid addition salts is in which the acid component itself does not have therapeutical effect in the applied dose or it does not have unfavorable influence on the effect of the active ingredient. These acid addition salts are pharmaceutically acceptable acid addition salts. The reason why acid addition salts, which do not belong to the pharmaceutically acceptable acid addition salts belong to the present invention is, that in given case they can be advantageous in the purification and isolation of the desired compounds.

Among the salts formed with bases especially important are the salts formed with alkali metals, e.g. sodium, potassium, alkaline-earth metals, e.g. calcium and magnesium, as well as with ammonia or organic amines. The latter bases can have further substituents, e.g. hydroxy or amino groups, which can influence e.g. the solubility and the handling of the product. The salts formed with bases are pharmaceutically acceptable base addition salts.

According to the invention the compounds of formula (I) can be synthesized by reacting a boronic acid derivative of formula (II)

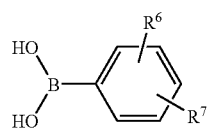

(II)

wherein the meaning of $R^6$ and $R^7$ are as described above—with 2-bromoaniline of formula (III)

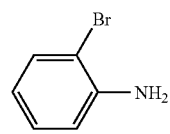

(III)

in the presence of a catalyst, preferably tetrakis(triphenylphosphine)-palladium(0), then the so obtained aminobiphenyl derivative of formula (IV)

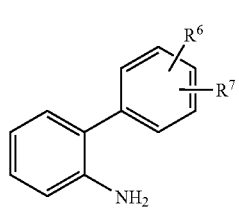

(IV)

wherein the meaning of $R^6$ and $R^7$ are as defined above—is sulfonylated with a sulfochloride derivative of formula (V)

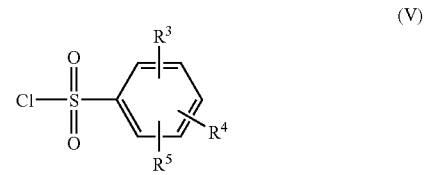

(V)

wherein the meaning of $R^3$, $R^4$ and $R^5$ are as defined above—and the formed sulfonamide derivative of formula

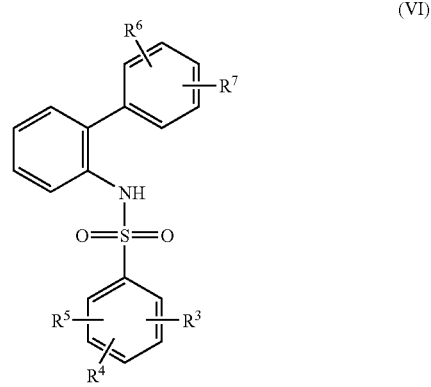

(VI)

wherein the meaning of $R^3$, $R^4$, $R^5$, $R^6$ and $R^7$ are as defined above—is submitted to cyclization reaction according to the method described in the literature [*J. Org. Chem.* 63 (1998) 5211-5215] and the obtained phenathridine acetic acid ester derivative of formula (VII)

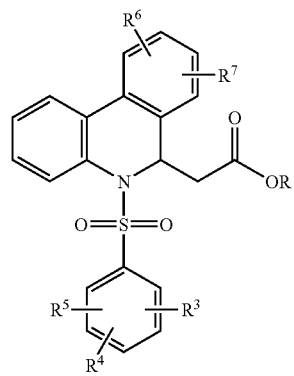

(VII)

wherein the meaning of $R^3$, $R^4$, $R^5$, $R^6$ and $R^7$ are as defined above and R is $C_1$-$C_4$ alkyl group—is hydrolyzed in the presence of a base to furnish a phenathridine acetic, acid derivative of formula (VIII)

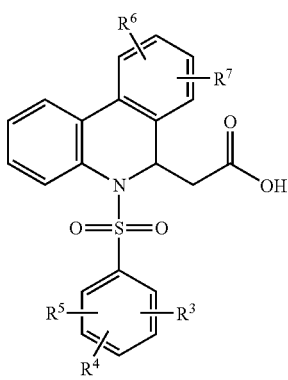

(VIII)

wherein the meaning of $R^3$, $R^4$, $R^5$, $R^6$ and $R^7$ are as defined above—then the latter is reacted with an amine derivative of formula (IX)

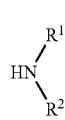

(IX)

wherein the meaning of $R^1$ and $R^2$ are as defined above—and the obtained phenanthridine derivative of formula (I) in given case can be transformed into an other compound of formula (I) by introducing new substituents and/or modifying or removing the existing ones, and/or salt formation and/or liberating the compound from salts.

The sulfonylation reaction is preferably carried out in a proper solvent, preferably in the presence of a base. The reactions are followed by thin layer chromatography. The necessary reaction time is 6-20 h. The work-up of the reaction mixture can be carried out by different methods.

a) The reaction mixture is concentrated and the product is isolated by crystallization or extraction. If the crude product is not pure enough, then column chromatography can be used for the purification of it. The column chromatography is carried out either on normal phase using Kieselgel 60 as adsorbent and different solvent systems, e.g. n-hexane/ethyl acetate, chloroform/methanol, dichloromethane/ethyl acetate or chloroform/acetone as eluents, or on reversed phase using YMC-Pack ODS-AQ type packings (produced by YMC) and acetonitrile/water/trifluoroacetic acid as eluent.

b) The reaction mixture is poured into ice-water and the product is isolated by filtration or extraction. The crude product is crystallized or purified by column chromatography as described above. The structures of the products are determined by IR, NMR and mass spectrometry.

The amide bond formation is preferably carried out by preparing an active derivative from a carboxylic acid of formula (VIII) which is reacted with an amine of formula (IX) preferably in the presence of a base.

The transformation of a carboxylic acid into an active derivative can be carried out in situ during the amide bond formation in a proper solvent (e.g. dimethylformamide, acetonitrile, chlorinated hydrocarbons or hydrocarbons). The active derivatives can be acid chlorides (e.g. prepared from carboxylic acid with thionyl chloride), mixed anhydrides (e.g. prepared from carboxylic acid with isobutyl chloroformate in the presence of a base, e.g. triethylamine), active esters (e.g. prepared from carboxylic acid with hydroxybenztriazol (HOBt) and dicyclohexyl-carbodiimide (DCC) or O-benzotriazol-1-yl-N,N,N',N'-tetramethyluronium hexafluorophosphate (HBTU) in the presence of a base e.g. triethylamine), acid azides (e.g. prepared from carboxylic acid hydrazide). The active derivatives can be prepared at a temperature in the range of 0° C. to room temperature. A proper amine of formula (IX) is added as a base or as a salt formed with inorganic acid to the so obtained solution or suspension in the presence of a base, e.g. triethylamine, needed for the liberation of the amine. The condensation reactions are followed by thin layer chromatography. The necessary reaction time is 6-20 h. The work-up of the reaction mixture can be carried out by different methods.

When the reaction mixture is a suspension, the precipitate is filtered off, washed with water and/or with an organic solvent and recrystallized from a proper solvent to give the pure product. If the crystallization does not lead to the pure product, then column chromatography can be used for the purification of it. The column chromatography is carried out on normal phase using Kieselgel 60 as adsorbent and different solvent systems, e.g. toluene/methanol, chloroform/methanol or toluene/acetone, as eluents or on reversed phase using YMC-Pack ODS-AQ type packings (produced by YMC) and acetonitrile/water/trifluoroacetic acid as eluent. If the reaction mixture is a solution at the end of the amide bond formation reaction, it is concentrated, and the residue is crystallized or extracted with a proper organic solvent and in given case purified by column chromatography as described above. The structures of the products are determined by IR, NMR and mass spectrometry.

The obtained amide derivatives of formula (I)—independently from the method of preparation—in given case can be transformed into another compound of formula (I) by introducing further substituents and/or modifying and/or removing the existing ones, and/or formation of salts with acids and/or liberating the benzamide derivative of formula (I) from the obtained acid addition salts by treatment with a base and/or the free sulfonamide derivative of formula (I) can be transformed into a salt by treatment with a base.

Boronic acids of formula (II) and sulfonyl chlorides of formula (V) are commercially available. Most of the amines of formula (IX) can be synthesized by different known methods. The syntheses of some new amines of formula (IX) are described in the Examples. Following these procedures the other amines of formula (IX) can also be prepared.

The compounds of the present invention and as well as their pharmaceutically acceptable salts or hydrates or solvates can be used as such or suitably in the form of pharmaceutical compositions. These compositions (drugs) can be in solid, liquid or semiliquid form and pharmaceutical adjuvant and auxiliary materials can be added, which are commonly used in practice, such as carriers, excipients, diluents, stabilizers, wetting or emulsifying agents, pH- and osmotic pressure-influencing, flavoring or aromatizing, as well as formulation-promoting or formulation-providing additives.

The dosage required to exert the therapeutical effect can vary within wide limits and will be fitted to the individual requirements in each of the particular case, depending on the stage of the disease, the condition and the bodyweight of the patient to be treated, as well as the sensitivity of the patient against the active ingredient, route of administration and number of daily treatments. The actual dose of the active ingredient to be used can safely be determined by the attending physician skilled in the art in the knowledge of the patient to be treated.

The pharmaceutical compositions containing the active ingredient according to the present invention usually contain 0.01 to 100 mg of active ingredient in a single dosage unit. It is, of course possible that the amount of the active ingredient in some compositions exceeds the upper or lower limits defined above.

The solid forms of the pharmaceutical compositions can be e.g. tablets, dragees, capsules, pills or lyophilized powder ampoules useful for the preparation of injections. Liquid compositions are the injectable and infusable compositions, fluid medicines, packing fluids and drops. Semiliquid compositions can be ointments, balsams, creams, shaking mixtures and suppositories.

For the sake of a simple administration it is suitable if the pharmaceutical compositions comprise dosage units containing the amount of the active ingredient to be administered once, or a few multiples or a half, third or fourth part thereof. Such dosage units are e.g. tablets, which can be powdered with grooves promoting the halving or quartering of the tablet in order to exactly administer the required amount of the active ingredient.

Tablets can be coated with an acid-soluble layer in order to assure the release of the active ingredient content after leaving the stomach. Such tablets are enteric-coated. A similar effect can be achieved also by encapsulating the active ingredient.

The pharmaceutical compositions for oral administration can contain e.g. lactose or starch as excipients, sodium carboxymethylcellulose, methylcellulose, polyvinyl pyrrolidine or starch paste as binders or granulating agents. Potato starch or microcrystalline cellulose is added as disintegration agents, but ultraamylopectin or formaldehyde casein can also be used. Talcum, colloidic silicic acid, stearin, calcium or magnesium stearate can be used as antiadhesive and lubricants.

The tablets can be manufactured e.g. by wet granulation, followed by pressing. The mixed active ingredients and excipients, as well as in given case part of the disintegrants are granulated with an aqueous, alcoholic or aqueous alcoholic solution of the binders in an appropriate equipment, then the granulate is dried. The other disintegrants, lubricants and antiadhesive agents are added to the dried granulate, and the mixture is pressed to a tablet. In given case the tablets are made with halving groove to ease the administration.

The tablets can be made directly from the mixture of the active ingredient and the proper auxiliaries by pressing. In given case, the tablets can be coated by using additives commonly used in the pharmaceutical practice, e.g. stabilizers, flavoring, coloring agents, such as sugar, cellulose derivatives (methyl- or ethylcellulose, sodium carboxymethylcellulose, etc), polyvinyl pyrrolidone, calcium phosphate, calcium carbonate, food coloring agents, food laces, aroma agents, iron oxide pigments, etc. In the case of capsules the mixture of the active ingredient and the auxiliaries is filled into capsules.

Liquid oral compositions, e.g. suspensions, syrups, elixirs can be made by using water, glycols, oils, alcohols, coloring and flavoring agents.

For rectal administration the composition is formulated in suppositories or clysters. The suppository can contain beside the active ingredient a carrier, so called adeps pro suppository. Carriers can be vegetable oils, such as hydrogenated vegetable oils, triglycerides of $C_{12}$-$C_{18}$ fatty acids (preferably the carriers under the trade name Witepsol). The active ingredient is homogeneously mixed with the melted adeps pro suppository and the suppositories are moulded.

For parenteral administration the composition is formulated as injection solution. For manufacturing the injection solution the active ingredients are dissolved in distilled water and/or in different organic solvents, such as glycolethers, in given case in the presence of solubilizers, e.g. polioxyethylensorbitane-monolaurate, -monooleate, or monostearate (Tween 20, Tween 60, Tween 80). The injection solution can also contain different auxiliaries, such as conserving agents, e.g. ethylendiamine tetraacetate, as well as pH adjusting agents and buffers and in given case local anaesthetic, e.g. lidocain. The injection solution containing the active ingredient of the invention is filtered before it is filled into ampoules, and it is sterilized after filling.

If the active ingredient is hygroscopic, then it can be stabilized by liophylization.

Bradykinin B1 receptor antagonists are described e.g. in the following international patent applications: WO200075107, WO02076964, WO04054584, WO02099388, WO05004810.

Utilities

The compounds of the present invention are bradykinin receptor antagonists, in particular selective bradykinin B1 receptor antagonists, consequently are useful in the treatment or prevention of painful and inflammatory processes. The compounds would be effective in the treatment of pain including, e.g., chronic pain, particularly inflamnuatory pain, hyperalgesia, bone and joint pain (osteoarthritis), repetitive motion pain, myofascial pain (muscular injury, fibromyalgia), visceral pain (ulcerative colitis, pancreatitis, cystitis, uveitis), perioperative pain (general surgery, gynecological), postoperative pain (postsurgical pain syndrome), posttraumatic pain (e.g. sprains or fracture), neuropathic pain (postherpetic neuralgia, nerve injury, phantom limb pain, mononeuropthy, polyneuropathy) dental pain, and cancer pain. Furthermore for the treatment of pain associated with angina, menstruation, diabetic vasculopathy, post capillary resistance or diabetic symptoms associated with insulitis (e.g. hyperglycemia, diuresis, proteinurea and increased nitrite and kallikrein urinary excretion), diabetic hyperalgeisa. Moreover the compounds may be used for the treatment angioedema, atherosclerosis, septic shock e.g. as anti-hypovolemic and/or anti-hypotensive agents, and sepsis. They may be used as smooth muscle relaxants for the treatment of spasm of the gastrointestinal tract or uterus. Further, the compounds of this invention can additionally be used to treat inflammatory skin disorders, such as psoriasis and eczema, and skin injuries including burning and sunburning (UV-erythema and pain). The compounds may be used to treat inflammatory pain of varied origins (e.g. rheumatoid arthritis, rheumatic disease, tenosynovitis, liver disease, irritable bowel syndrome, inflammatory bowel disease, Crohn's disease, nephritis, allergic rhinitis, vasomotor rhinitis, uveitis, gingivitis), allergies. Such compounds may be used therapeutically to treat inflammatory airways disease e.g. chronic obstructive pulmonary disease, adult respiratory distress syndrome, bronchitis, pneumonia, asthma. They may be used to control, restrict or reverse airways hyperreactivity in asthma, to treat intrinsic and extrinsic asthma including allergic asthma (atopic or non-atopic), occupational asthma, viral or bacterial exacerbated asthma, other non-allergic asthmas, "wheezy-infant syndrome", as well as exercise-induced bronchoconstriction. They may be effective against pneuiloconiosis, including aluminosis, antracosis, asbestosis, chalicosis, ptilosis, siderosis, silicosis, tabacosis and byssinosis. Additionally, they may be effective in some neurological disorders, e.g. against multiple sclerosis, Alzheimer's disease, epilepsy, cerebral edema, headache including cluster headache, migraine including prophylactic and acute use, as well as closed head trauma.

Biological Evaluation
Assessment of Antagonist Potency at B1 and B2 Receptors In Vitro by Measurement of Cytosolic Calcium Ion Concentration with a Plate Reader Fluorimeter in Cells Expressing Recombinant Human B1 or B2 Receptors Cell Culture Chinese hamster ovary (CHO) cells stably expressing recombinant human B1 (CHO-B1, Euroscreen) or B2 (CHO-B2, Perkin-Elmer) receptors were cultured in Dulbecco's Modified Eagle's Medium (DMEM) containing 10% Fetal Calf Serum (FCS), 100 U/ml penicillin, 0.1 mg/ml streptomycin, 0.25 µg/ml amphotericin B, 1% Minimum Essential Medium Eagle (MEM), non essential amino acid solution, 600 µg/ml G418, 1% pyruvate (for the B2 cell line). Cells were kept at 37° C. in a humidified incubator in an atmosphere of 5% $CO_2$/95% air and were passaged 1:4 three times a week. Cells were plated at $1.5$-$2.5 \times 10^4$ cell/well on standard 96-well microplates, measurements of cytosolic calcium ion concentration ($[Ca^{2+}]_i$) were carried out 1-2 days after cell plating.

Fluorimetric Measurement of Cytosolic Calcium Concentration

Measurements of $[Ca^{2+}]_i$ were carried out on CHO-B1 and CHO-B2 cells stably expressing human B1 and B2 receptors, respectively. Cells were grown in standard 96-well microplates and before the measurement were loaded with a fluorescent $Ca^{2+}$-sensitive dye, fluo-4/AM (2 µM): after removing the culture medium the dye was added to the cells (dissolved in assay buffer: 145 mM NaCl, 5 mM KCl, 2 mM $MgCl_2$, 2 mM $CaCl_2$, 10 mM HEPES, 20 mM D-glucose, 2 mM probenecid, 100 µl/well) and cells were incubated at 37° C. in a humidified incubator in an atmosphere of 5% $CO_2$/95% air for 40-120 min. To stop dye loading cells were washed twice with assay buffer. After washing, various concentrations of the test compounds (diluted in extracellular medium from a DMSO stock solution, final DMSO concentration was <0.1%) or buffer were added to each well depending on the experimental setup. After incubation at 37° C. for 20-25 min. baseline and agonist-evoked changes of $[Ca^{2+}]_i$ were measured column by column with a plate reader fluorimeter (Fluoroskan Ascent, Labsystems). Excitation and detection of emission was carried out from the bottom of the plate. Filters used for Fluo-4: excitation filter ~485 nm, emission filter ~538 nm. The whole measurement process was performed at 37° C. and was controlled by custom software. Inhibitory potency of the test compounds was assessed by measuring the reduction in the agonist-evoked $[Ca^{2+}]_i$-elevation in the presence of different concentrations of the compounds. The agonists were LysDABK for CHO-B1, and bradykinin for CHO-B2 cells. Agonists were applied at an $EC_{80}$ concentration, the $EC_{80}$-values were derived from daily determined dose-response curves. Fluorescence data were expressed as ΔF/F (fluorescence change normalized to baseline). All treatments on a single plate were measured in multiple wells. Data from all wells with the same treatment were averaged and the average values were used for analysis. Inhibitory potency of a compound at a single concentration point was expressed as percent inhibition of the control agonist response. Sigmoidal concentration-inhibition curves were fitted to the data (derived from at least three independent experiments) and $IC_{50}$-values were determined as the concentration that produces half of the maximal inhibition caused by the compound.

In Table 1 the most effective compounds of this invention and some of the examined reference compounds measured in this test are listed.

TABLE 1

| Number of example | B1 func. | Code of reference compound | B1 func. |
|---|---|---|---|
| 1 | +++ | 70002460 | ++ |
| 2 | +++ | 70003770 | + |
| 3 | +++ | 70004287 | +++ |
| 4 | +++ | 70004387 | ++ |
| 5 | +++ | | |
| 6 | +++ | | |
| 8 | ++ | | |
| 9 | +++ | | |
| 14 | +++ | | |
| 15 | +++ | | |
| 16 | +++ | | |
| 17 | +++ | | |
| 18 | +++ | | |
| 19 | ++ | | |
| 20 | +++ | | |
| 21 | +++ | | |

+ $IC_{50}$ > 0.5 µM
++ $IC_{50}$ is between 0.1 and 0.5 µM
+++ $IC_{50}$ < 0.1 µM The reference compounds are as follows:

70002460: 4-{2-[(2,2-diphenyl-ethyl)-amino]-5-{[4-/(4-<1-methyl-ethyl>-1-piperazinyl)-carbonyl/-1-piperidinyl]-sulfonyl}-benzoyl}-morpholine [Patent No. WO200075107]

70003770: (±)-N-[1-(4-aminomethyl-benzyl)-2-oxo-2-pyrrolidin-1-yl-ethyl]-3-(naphthalene-2-sulfonylamino)-3-phenyl-propionamide [Patent No. WO02076964]

70004287: 2-[1-(3,4-dichloro-benzenesulfonyl)-3-oxo-1,2,3,4-tetrahydroquinoxalin-2(R)-yl]-N-{2-[4-(4,5-dihydro-1H-imidazol-2-yl)-phenyl]-ethyl}-acetamide [Patent No. WO04054584]

70004387: (±)-N-[4-(1,4'-bipiperidin)-1'-yl-phenyl]-N'-[2,3-dihydro-5-(4-methyl-phenyl)-2-oxo-1-propyl-1H-1,4-benzodiazepin-3-yl]-urea [Patent No. WO02099388]

Receptor Binding Assays

1. Human Recombinant Bradykinin B1 Receptor Binding

Binding assays were carried out on human recombinant bradykinin1 receptors (expressed in CHO cells) according to the Euroscreen Technical Data Sheet (Cat. No.: ES-091). 20 µg protein/tube was incubated with [3,4-prolyl-3,4-$^3$H(N)]-[Des-Arg$^{10}$] Kallidin as radioligand. Non specific binding was determined in the presence of 10 µM Lys-des-Arg$^9$-Bradykinin. The final incubation volume was 250 µl. Samples were incubated for 15 min. at 25° C. then were rapidly vacuum filtered through GF/B filters presoaked for at least 1 h in 0.5% PEI. Radioactivity was determined by liquid scintillation spectroscopy.

In Table 2 the most effective compounds of this invention and some of the examined reference compounds measured in this test are listed.

TABLE 2

| Number of example | B1 binding | Code of reference compound | B1 binding |
|---|---|---|---|
| 1 | +++ | 70002460 | +++ |
| 2 | +++ | 70003770 | + |
| 3 | +++ | 70004287 | +++ |
| 4 | +++ | 70004387 | +++ |
| 5 | +++ | | |
| 6 | +++ | | |
| 8 | +++ | | |
| 9 | +++ | | |
| 14 | +++ | | |

TABLE 2-continued

| Number of example | B1 binding | Code of reference compound | B1 binding |
|---|---|---|---|
| 15 | +++ | | |
| 16 | +++ | | |
| 17 | +++ | | |
| 18 | +++ | | |
| 19 | +++ | | |
| 20 | +++ | | |
| 21 | +++ | | |

+ $K_i$ > 0.5 μM
++ $K_i$ is between 0.1 and 0.5 μM
+++ $K_i$ < 0.1 μM

The reference compounds are as follows:

70002460: 4-{2-[(2,2-diphenyl-ethyl)-amino]-5-{[4-/(4-<1-methyl-ethyl>-1-piperazinyl)-carbonyl/-1-piperidinyl]-sulfonyl}-benzoyl}-morpholine [Patent No. WO200075107]
70003770: (±)-N-[1-(4-aminomethyl-benzyl)-2-oxo-2-pyrrolidin-1-yl-ethyl]-3-(naphthalene-2-sulfonylamino)-3-phenyl-propionamide [Patent No. WO02076964]
70004287: 2-[1-(3,4-dichloro-benzenesulfonyl)-3-oxo-1,2,3,4-tetrahydroquinoxalin-2(R)-yl]-N-{2-[4-(4,5-dihydro-1H-imidazol-2-yl)-phenyl]-ethyl}-acetamide [Patent No. WO04054584]
70004387: (±)-N-[4-(1,4'-bipiperidin)-1'-yl-phenyl]-N'-[2,3-dihydro-5-(4-methyl-phenyl)-2-oxo-1-propyl-1H-1,4-benzodiazepin-3-yl]-urea [Patent No. WO02099388]

2. Human Recombinant Bradykinin B2 Receptor Binding

Binding assays were carried out on human recombinant bradykinin2 receptors (expressed in CHO cells) according to the Receptor Biology Technical Data Sheet (Cat. No.: RBHB2M) with minor modifications. 8.4 μg protein/tube was incubated with [2,3,-prolyl-3,4-$^3$H(N)]-Bradykinin as radioligand. Non specific binding was determined in the presence of 5 μM bradykinin. The final incubation volume was 200 μl. Samples were incubated for 90 min. at +4° C. then were rapidly vacuum filtered through GF/B filters presoaked for at least 1 h in 0.5% PEI. Radioactivity was determined by liquid scintillation spectroscopy.

The compounds exhibited high affinity and selectivity (>50 fold) for the human B1 receptor over the human B2 receptor according to both functional and binding assays.

The synthesis of compounds and pharmaceutical compositions according to the invention is illustrated by the following not limiting Examples.

REFERENCE EXAMPLE 1

2-(4-Pyridin-4-yl-piperazin-1-yl)-ethylamine a) 2-[2-(4-Pyridin-4-yl-piperazin-1-yl)-ethyl]-isoindole-1,3-dione A mixture of 1-pyridin-4-yl-piperazine [*Org. Lett.* 4 (2002) 737-740] (1.0 g, 6.12 mmol), N-(2-bromoethyl)-phthalimide (1.71 g, 6.74 mmol), potassium carbonate (0.85 g, 6.12 mmol), potassium iodide (1.02 g, 6.12 mmol) and dimethyl formamide (10 mL) was stirred at 70° C. for 24 h, then concentrated. The residue was dissolved in water, extracted with dichloromethane, the organic layer was dried over sodium sulfate, filtered and concentrated. The crude product was purified by column chromatography using Kieselgel 60 (0.040-0.063 mm) (Merck) as adsorbent, and chloroform:methanol:NH$_4$OH=10:1:0.1 as eluent to yield 1.52 g (74%) of the title compound, as a white solid.

b) 2-(4-Pyridin-4-yl-piperazin-1-yl)-ethylamine

A stirred mixture of 2-[2-(4-pyridin-4-yl-piperazin-1-yl)-ethyl]-isoindole-1,3-dione (1.52 g, 4.52 mmol), ethanol (47.5 mL), water (2.5 mL) and hydrazine hydrate (98%, 0.438 mL, 9.04 mmol) was refluxed for 3 h, then cooled and diluted with diethyl ether (100 mL). The precipitated crystals were filtered off, washed with diethyl ether and filtrate was concentrated. The residue was dissolved N sodium hydroxide (25 mL), extracted with dichloromethane (4×25 mL), the combined organic layers were washed with brine (25 mL), dried over sodium sulfate, filtered and concentrated to yield 0.58 g (62%) of the title compound as a colorless oil.

REFERENCE EXAMPLE 2

2-[4-(4,5-Dihydro-1H-imidazol-2-yl)-phenyl]-ethylamine dihydrochloride a) 4-[2-(1,3-Dioxo-1,3-dihydro-isoindol-2-yl)-ethyl]-benzonitrile Under argon, a solution of 4-(2-hydroxy-ethyl)-benzonitrile [*Helv. Chim. Acta* 64 (1981) 1688-1703] (4.49 g, 30.5 mmol), phthalimide (4.94 g, 33.55 mmol), triphenylphosphine (8.8 g, 33.55 mmol) and dimethyl formamide (100 mL) was stirred at 0° C. for 20 minutes, then diethyl azodicarboxylate (7.59 mL, 48.8 mmol) was added dropwise at 0° C. The so obtained reaction mixture was stirred at room temperature overnight, then poured into ice-water (740 mL). The precipitated product was filtered off, washed with water and dried. The crude product was recrystallized from 2-propanol to yield 7.83 g (93%) of the title compound as a yellow solid.

b) 2-{2-[4-(4,5-Dihydro-1H-imidazol-2-yl)-phenyl]-ethyl}-isoindole-1,3-dione

Dry hydrogen chloride gas was bubbled through an ice cold solution of 4-[2-(1,3-dioxo-1,3-dihydro-isoindol-2-yl)-ethyl]-benzonitrile (7.83 g, 28.3 mmol) in ethanol (400 mL) for 3 h, then the so obtained mixture was kept at 8° C. overnight. The reaction mixture was concentrated in vacuo, the residue was dissolved in dry ethanol (400 mL), ethylenediamine (2.0 mL, 29.7 mmol) was added and the reaction mixture was stirred at room temperature overnight. The mixture was concentrated in vacuo, the residue was partitioned between dichloromethane (400 mL) and concentrated ammonium hydroxide (400 mL), the phases were separated and the water phase was extracted with dichloromethane (2×200 mL). The combined organic layers were dried over sodium sulfate, filtered and concentrated. The crude product was recrystallized from 2-propanol to yield 5.58 g (62%) of the title compound as a white solid.

c) 2-[4-(4,5-Dihydro-1H-imidazol-2-yl)-phenyl]-ethylamine dihydrochloride

A mixture of 2-{2-[4-(4,5-dihydro-1H-imidazol-2-yl)-phenyl]-ethyl}-isoindole-1,3-dione (5.58 g, 17.47 mmol), ethanol (140 mL) and hydrazine hydrate (98%, 6.57 mL, 135.4 mmol) was stirred at room temperature for 2 h, then concentrated in vacuo. The residue was partitioned between dichloromethane (250 mL) and N sodium hydroxide (250 mL), the phases were separated and the water phase was extracted with dichloromethane (6×250 mL). The combined organic layers were dried over sodium sulfate, filtered and concentrated. The crude product was dissolved in methanol (15 mL), the pH of the solution was adjusted to 5 by addition of methanolic solution of hydrogen chloride, then the mixture was stirred at room temperature for 1 h. After addition of diethyl ether (200 mL) the suspension was stirred at 0° C. for 2 h, the precipitated crystals were filtered off, washed with diethyl ether and dried to yield 4.11 g (90%) of the title compound as a white solid.

REFERENCE EXAMPLE 3

(3-[1,4']Bipiperidinyl-1'-yl)-propylamine trihydrochloride a) (3-[1,4']Bipiperidinyl-1'-yl-propyl-carbamic acid tert-butyl ester A mixture of 4-piperidinopiperidine (Aldrich) (2.0 g, 11.88 mmol), (3-bromo-propyl)-carbamic acid tert-butyl ester [Eur. J. Med. Chem. Chim. Ther. 37 (2002) 573-584] (3.96 g, 16.63 mmol), dimethyl formamide (130 mL) and potassium carbonate (1.64 g, 11.88 mmol) was stirred at room temperature overnight, then concentrated in vacuo. The residue was dissolved in water (150 mL), extracted with dichloromethane (3×150 mL), the combined organic layers were washed with brine (150 mL), dried over sodium sulfate, filtered and concentrated. The crude product was submitted to column chromatography using Kieselgel 60 (0.040-0.063 mm) (Merck) as adsorbent, and chloroform:methanol:NH$_4$OH=10:1:0.1 as eluent to yield 2.27 g (59%) of the title compound as an oil.

b) 3-[1,4']Bipiperidinyl-1'-yl)-propylamine trihydrochloride

A mixture of (3-[1,4']bipiperidinyl-1'-yl-propyl)-carbamic acid tert-butyl ester (2.15 g, 6.6 mmol), dry dioxane (40 mL) and 6.5 N hydrogen chloride in dioxane (22 mL) was stirred at room temperature overnight, then diluted with diethyl ether and stirred at 0° C. for 1 h. The precipitated crystals were filtered off, washed with diethyl ether and dried to yield 2.03 g (92%) of the title compound as a beige solid.

REFERENCE EXAMPLE 4 trans-4-(2-Pyrrolidin-1-yl-ethyl)-cyclohexylamine dihydrochloride a) trans-2-{1-[4-(N-tert-butoxycarbonyl)-amino]-cyclohexyl}-ethanol A solution of trans-2-{1-[4-(N-tert-butoxycarbonyl)-amino]-cyclohexyl}-acetic acid methyl ester [J. Med. Chem. 43 (2000) 1878-1885] (28.5 g, 105.2 mmol) in dry tetrahydrofuran (500 mL) was cooled to −2° C., lithium aluminum hydride (5.4 g, 142 mmol) was added portionwise and the mixture was stirred at −2° C. for 60 minutes. The reaction mixture was cooled to −10° C. and quenched with ethyl acetate (15 mL), then brine (43 ml) was slowly added to the mixture at 0° C. The precipitated salts were filtered, and washed with ethyl acetate. The filtrate was concentrated in vacuo. The residue was recrystallized from diisopropyl ether (100 ml) to yield 23.7 g (93%) of the title compound as a white powder.

b) Methanesulfonic acid trans-2-(4-tert-butoxycarbonylamino-cyclohexyl)-ethyl ester To a stirred solution of trans-2-{1-[4-(N-tert-butoxycarbonyl)-amino]-cyclohexyl}-ethanol (15 g, 62 mmol), and triethylamine (10.5 mL, 75 mmol) in dry dichloromethane (150 mL) methanesulfonyl chloride (5.7 mL, 73.4 mmol) in dichloromethane (25 mL) was added dropwise at 0° C. After stirring 30 minutes at 0° C., the solution was extracted three times with water. The organic solution was dried over sodium sulfate and concentrated in vacuo to yield 13.0 g (65%) of the title compound.

c) trans-[4-(2-Pyrrolidin-1-yl-ethyl)-cyclohexyl]-carbamic acid tert-butyl ester A mixture of methanesulfonic acid trans-2-(4-tert-butoxycarbonylamino-cyclohexyl)-ethyl ester (3.2 g, 10 mmol), potassium carbonate (1.4 g, 10 mmol) and pyrrolidine (1.25 mL, 15 mmol) in acetonitrile (40 mL) was stirred at 60° C. for 2 hours. The mixture was cooled to room temperature and poured into water (200 mL). The precipitated white crystals were filtered off and washed with water to yield 1.9 g (64%) of the title compound.

d) trans-4-(2-Pyrrolidin-1-yl-ethyl)-cyclohexylamine dihydrochloride

The title compound was prepared from trans-[4-(2-pyrrolidin-1-yl-ethyl)-cyclohexyl]-carbamic acid tert-butyl ester according to the method described in Reference Example 3/b.

REFERENCE EXAMPLE 5

2-(4-Pyridin-2-yl-piperazin-1-yl)-ethylamine tetrahydrochloride a) 2-(4-Pyridin-2-yl-piperazin-1-yl)-ethanol trihydrochloride A stirred mixture of 1-(2-pyridyl)-piperazine (Aldrich) (4.6 mL, 30 mmol), 2-bromoethanol (2.5 mL, 35 mmol), potassium carbonate (4.8 g, 35 mmol) and 1-butanol (60 mL) was refluxed overnight, then further amount of 2-bromoethanol (2.5 mL, 35 mmol) was added and the mixture was refluxed for 24 h. After cooling to room temperature the precipitated salts were filtered off, washed with ethyl acetate and the filtrate was concentrated. The residue was dissolved in ethyl acetate (150 mL) and extracted with water (150 mL). The organic layer was dried over sodium sulfate, filtered and concentrated. The residue was dissolved in diethyl ether (100 mL), the pH of the solution was adjusted to 5 by addition of a solution of hydrogen chloride in ethyl acetate, then the mixture was stirred at room temperature for 1 h. After addition of diethyl ether (150 mL) the suspension was stirred at 0° C. for 2 h, the precipitated crystals were filtered off, washed with diethyl ether and dried to yield 4.8 g (50%) of the title compound.

b) 2-[2-(4-Pyridin-2-yl-piperazin-1-yl)-ethyl]-isoindole-1,3-dione

The title compound was prepared from 2-(4-pyridin-2-yl-piperazin-1-yl)-ethanol (liberated from trihydrochloride salt with 10% sodium hydroxide solution and extracted with dichloromethane) according to the method described in Reference Example 2/a.

c) 2-(4-Pyridin-2-yl-piperazin-1-yl)-ethylamine tetrahydro chloride

The title compound was prepared from 2-[2-(4-pyridin-2-yl-piperazin-1-yl)-ethyl]-isoindole-1,3-dione according to the method described in Reference Example 2/c.

REFERENCE EXAMPLE 6

4-[4-(4,5-Dihydro-1H-imidazol-2-yl)-benzyl]-piperidine a) (4-Cyano-benzyl)-phosphonic acid diethyl ester A mixture of 4-cyano-benzyl bromide (41.8 g, 0.213 mol) and triethyl phosphite (42 mL, 0.244 mol) was stirred in a flask equipped with a Dean-Stark trap at 150° C. for 6 h, then the reaction mixture was submitted to distillation in vacuo to yield 52.2 g (97%) of the title compound.

b) 4-(1-Benzyl-piperidin-4-ylidenemethyl)-benzonitrile

Under argon, to a stirred mixture of N-benzyl-4-piperidone (Aldrich) (26.0 g, 0.137 mol) and (4-cyano-benzyl)-phosphonic acid diethyl ester (36.6 g, 0.1445 mol) in dimethylformamide (260 mL) sodium hydride (60%, 7.8 g, 0.195 mol) was added at 0° C. The reaction mixture was stirred at room temperature overnight, then ethanol (10 mL) was added dropwise, the so obtained mixture was poured into water (300 mL), and extracted with diethyl ether (3×300 mL). The organic layer was dried over sodium sulfate and concentrated. The residue was purified by column chromatography using Kieselgel 60 (0.040-0.063 mm) (Merck) as adsorbent, and n-hexane:ethyl acetate=2:1 as eluent to yield 34.65 g (87%) of the title compound as an oil.

c) 4-(1-Benzyl-piperidin-4-ylidenemethyl)-benzimidic acid ethyl ester

A mixture of 4-(1-benzyl-piperidin-4-ylidenemethyl)-benzonitrile (14 g, 48.6 mmol), chloroform (10 mL) and 6 M hydrogen chloride in ethanol (300 mL) was stirred at room temperature for 48 hours. The solution was concentrated in vacuo, the remaining solid was repeatedly dissolved in ethanol (400 mL) and concentrated in vacuo to yield 16.4 g (92.4%) of the title compound, which was used in the next steps without further purification.

d) 1-Benzyl-4-[4-(4,5-dihydro-1H-imidazol-2-yl)-benzylidene]-piperidine

To a solution of 4-(1-benzyl-piperidin-4-ylidenemethyl)-benzimidic acid ethyl ester (6.8 g, 18.3 mmol) in ethanol (250 mL) ethylenediamine (2.45 mL, 36.6 mmol) was added and the mixture was stirred at room temperature overnight. The precipitated solid was filtered off, and the filtrate was concentrated in vacuo. The residue was repeatedly dissolved in ethanol (100 mL) and concentrated in vacuo. The crude product was purified by flash column chromatography using Kieselgel 60 (0.015-0.040 mm) as adsorbent (Merck) and chloroform:methanol:NH$_4$OH=9:2:0.1 as eluent to yield 2.7 g (44.6%) of the title compound.

e) 4-[4-(4,5-Dihydro-1H-imidazol-2-yl)-benzyl]-piperidine

To a stirred solution of 1-benzyl-4-[4-(4,5-dihydro-1H-imidazol-2-yl)-benzylidene]-piperidine (0.1 g, 0.3 mmol) in ethanol (20 mL), ammoniumformate (0.19 g, 3 mmol) and 10% Pd/C (20 mg) were added ad the mixture was refluxed for 8 hours. The catalyst was filtered off, and the filtrate was concentrated in vacuo. The remaining crude material was purified by column chromatography using basic aluminum oxide (150 mesh, Aldrich) as adsorbent and 10% methanol in chloroform as eluent to yield 68 mg (92%) of the title compound.

REFERENCE EXAMPLE 7

2-(4-Piperidin-4-ylmethyl-phenyl)-1,4,5,6-tetrahydro-pyrimidine a) 2-[4-(1-Benzyl-piperidin-4-ylidenemethyl-phenyl]-1,4,5,6-tetrahydro-pyrimidine The title compound was prepared from 4-(1-benzyl-piperidin-4-ylidenemethyl)-benzimidic acid ethyl ester and 1,2-diamino-propane according to the method described in Reference Example 6/d.

b) 2-(4-Piperidin-4-ylmethyl-phenyl)-1,4,5,6-tetrahydro-pyrimidine

The title compound was prepared from 2-[4-(1-benzyl-piperidin-4-ylidenemethyl)-phenyl]-1,4,5,6-tetrahydro-pyrimidine according to the method described in Reference Example 6/e.

REFERENCE EXAMPLE 8

2-(4-Pyridin-4-yl-piperazin-1-yl)-propylamine a) 2-[2-(4-Pyridin-4-yl-piperazin-1-yl)-propyl]-isoindole-1,3-dione The title compound was prepared from 1-pyridin-4-yl-piperazine [Org. Lett. 4 (2002) 737-740] and N-(2-bromopropyl)-phthalimide according to the method described in Reference Example 1/a.

b) 2-(4-Pyridin-4-yl-piperazin-1-yl)-propylamine

The title compound was prepared from 2-[2-(4-pyridin-4-yl-piperazin-1-yl)-propyl]-isoindole-1,3-dione according to the method described in Reference Example 1/b.

EXAMPLE 1

2-[5-(3,4-Dichloro-benzenesulfonyl)-8-fluoro-5,6-dihydro-phenanthridin-6-yl]-N-{2-[4-(4,5-dihydro-1H-imidazol-2-yl)-phenyl]-ethyl}-acetamide hydrochloride a) 4'-Fluoro-biphenyl-2-ylamine To a stirred solution of 2-bromoaniline (1.72 g, 10.0 mmol) in diglyme (30 mL) tetrakis(triphenylphosphine)-palladium (0) (0.13 g, 0.3 mmol) and 2.0 M aqueous sodium carbonate solution (15 mL, 30.0 mmol) were added. In a separate flask, 4-fluorophenylboronic acid (2.23 g 16.0 mmol) was dissolved in ethanol (8 mL) and the mixture containing 2-bromoaniline was added to this boronic acid solution. The obtained brown reaction mixture was heated at 80° C. for 6 hours, then cooled, diluted with ethyl acetate and washed with saturated ammonium chloride solution. The organic layer was dried over sodium sulfate, filtered and concentrated. The residue was purified by flash column chromatography using Kieselgel 60 (0.015-0.040 mm) as adsorbent (Merck) and n-hexane:ethyl-acetate=2:1 as eluent to yield after recrystallization from ethanol 1.8 g (60%) of the title compound as white crystals.

b) 3,4-Dichloro-N-(4'-fluoro-biphenyl-2-yl-benzenesulfonamide

To a stirred solution of 4'-fluoro-biphenyl-2-ylamine (2.17 g 11.6 mmol) and 4-dimethylaminopyridine (13 mg, 0.11 mmol) in pyridine (20 mL) 3,4-dichloro-benzenesulfonyl chloride (4.23 g 17.4 mmol) was added at 0° C. The reaction mixture was stirred at room temperature overnight, then concentrated. The residue was partitioned between chloroform (50 mL) and water (50 mL). The aqueous layer was separated and extracted with chloroform (2×50 mL). The combined organic extracts were washed with saturated aqueous sodium bicarbonate (20 mL) and brine (20 mL) dried over sodium sulfate, filtered and concentrated. The product was crystallized from 2-propanol to yield 3.58 g (78%) of the title compound as white crystals.

c) [5-(3,4-Dichloro-benzenesulfonyl)-8-fluoro-5,6-dihydro-phenanthridin-6-yl]-acetic acid methyl ester Sodium acetate (370 mg, 4.5 mmol) was dried in a 100 mL two-necked flask at 150° C. in vacuo for 2 hours, then palladium acetate (100.8 mg 0.45 mmol), copper(II) acetate hydrate (90.0 mg, 0.45 mmol), 3,4-dichloro-N-(4'-fluoro-biphenyl-2-yl)-benzenesulfonamide (3.58 g, 9 mmol), methyl acrylate (2.32 g, 27 mmol), 4 Å molecular sieves (3.6 g) and dimethyl formamide (45 mL) were added, and the resulting mixture was stirred at 120° C. for 16 hours. After cooling the reaction mixture was concentrated, then diluted with water (50 mL) and extracted with diethyl ether (2×30 mL), dried over sodium sulfate, filtered and concentrated. The residue was purified by flash column chromatography using Kieselgel 60 (0.015-0.040 mm) as adsorbent (Merck) and n-hexane: ethyl-acetate=4:1 as eluent to yield 1.91 g (44%) of the title compound as white crystals.

d) [5-(3,4-Dichloro-benzenesulfonyl)-8-fluoro-5,6-dihydro-phenanthridin-6-yl]-acetic acid To a stirred solution of [5-(3,4-dichloro-benzenesulfonyl)-8-fluoro-5,6-dihydro-phenanthridin-6-yl]-acetic acid methyl ester (0.48 g, 1 mmol) in a 1:1 mixture of tetrahydrofuran and water (30 mL) lithium hydroxide monohydrate (105 mg, 2.5 mmol) was added. The reaction mixture was stirred at room temperature for 2 hours, then concentrated. The residue was dissolved in a mixture of ethyl acetate (25 mL) and water (25 mL) and acidified with 1N hydrochloride solution. The aqueous phase was separated and extracted with ethyl acetate (2×25 mL). The combined organic extracts were dried over sodium sulfate, filtered and concentrated to yield 0.46 g (98%) of the title compound as white crystals.

e) 2-[5-(3,4-Dichloro-benzenesulfonyl)-8-fluoro-5,6-dihydro-phenanthridin-6-yl]-N-{2-[4-(4,5-dihydro-1H-imidazol-2-yl)-phenyl]-ethyl}-acetamide hydrochloride A solution of [5-(3,4-dichloro-benzenesulfonyl)-8-fluoro-5,6-dihydro-phenanthridin-6-yl]-acetic acid (210 mg, 0.45 mmol), triethylamine (0.07 mL, 1.5 mmol) and N-(3-dimethylaminopropyl)-N'-ethylcarbodiimide hydrochloride (0.19 g, 0.5 mmol) in dry dimethyl formamide (5 mL) was stirred at room temperature for five minutes before 2-[4-(4,5-dihydro-1H-imidazol-2-yl)-phenyl]-ethylamine dihydrochloride (Reference Example 2) (131 mg, 0.5 mmol) was added. The pH of the reaction mixture was adjusted to 8 by addition of triethylamine, the so obtained mixture was stirred at room temperature overnight, then concentrated in vacuo. The residue was purified by preparative thin-layer chromatography (dichloromethane:methanol:NH$_4$OH=5:1:0.1) to yield 382 mg (75%) of the title compound as white crystals. MS (EI) 638.1 (MH$^+$).

EXAMPLE 2

2-[5-(3,4-Dichloro-benzenesulfonyl)-5,6-dihydro-phenanthridin-6-yl]-N-{2-[4-(4,5-dihydro-1H-imidazol-2-yl)-phenyl]-ethyl}-acetamide hydrochloride a) N-Biphenyl-2-yl-3,4-dichloro-benzenesulfonamide The title compound was prepared from 2-aminobiphenyl (Aldrich) according to the method described in Example 1b.

b) [5-(3,4-Dichloro-benzenesulfonyl)-5,6-dihydro-phenanthridin-6-yl]-acetic acid methyl ester The title compound was prepared from N-biphenyl-2-yl-3,4-dichloro-benzenesulfonamide according to the method described in Example 1c.

c) [5-(3,4-Dichloro-benzenesulfonyl)-5,6-dihydro-phenanthridin-6-yl]-acetic acid The title compound was prepared from [5-(3,4-dichloro-benzenesulfonyl)-5,6-dihydro-phenanthridin-6-yl]-acetic acid methyl ester according to the method described in Example 1d.

d) 2-[5-(3,4-Dichloro-benzenesulfonyl)-5,6-dihydro-phenanthridin-6-yl]-N-{2-[4-(4,5-dihydro-1H-imidazol-2-yl)-phenyl]-ethyl}-acetamide hydrochloride The title compound was prepared from [5-(3,4-dichloro-benzenesulfonyl)-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e. MS (EI) 620.5 (MH$^+$).

EXAMPLE 3

2-[5-(3,4-Dichloro-benzenesulfonyl-5,6-dihydro-phenanthridin-6-yl]-N-[2-(4-pyridin-4-yl-piperazin-1-yl)-ethyl]-acetamide The title compound was prepared from [5-(3,4-dichloro-benzenesulfonyl)-5,6-dihydro-phenanthridin-6-yl]-acetic acid (Example 2c) and 2-(4-pyridin-4-yl-piperazin-1-yl)-ethylamine (Reference Example 1) according to the method described in Example 1e. MS (EI) 637.3 (MH$^+$).

EXAMPLE 4 trans-2-[5-(3,4-Dichloro-benzenesulfonyl)-5,6-dihydro-phenanthridin-6-yl]-N-[4-(2-pyrrolidin-1-yl-ethyl)-cyclohexyl]-acetamide The title compound was prepared from [5-(3,4-dichloro-benzenesulfonyl)-5,6-dihydro-phenanthridin-6-yl]-acetic acid (Example 2c) and trans-4-(2-pyrrolidin-1-yl-ethyl)-cyclohexylamine dihydrochloride (Reference Example 4) according to the method described in Example 1e. MS (EI) 627.2 (MH$^+$).

EXAMPLE 5

2-[5-(3,4-Dichloro-benzenesulfonyl)-5,6-dihydro-phenanthridin-6-yl]-1-{4-[4-(4,5-dihydro-1H-imidazol-2-yl)-benzyl]-piperidin-1-yl}-ethanone The title compound was prepared from [5-(3,4-dichloro-benzenesulfonyl)-5,6-dihydro-phenanthridin-6-yl]-acetic acid (Example 2c) and 4-[4-(4,5-dihydro-1H-imidazol-2-yl)-benzyl]-piperidine (Reference Example 6) according to the method described in Example 1e. MS (EI) 674.3 (MH$^+$).

EXAMPLE 6

2-[5-(3,4-Dichloro-benzenesulfonyl)-5,6-dihydro-phenanthridin-6-yl]-1-{4-[4-(1,4,5,6-tetrahydro-pyrimidin-2-yl)-benzyl]-piperidin-1-yl}-ethanone The title compound was prepared from [5-(3,4-dichloro-benzenesulfonyl)-5,6-dihydro-phenanthridin-6-yl]-acetic acid (Example 2c) and 2-(4-piperidin-4-ylmethyl-phenyl)-1,4,5,6-tetrahydro-pyrimidine (Reference Example 7) according to the method described in Example 1e. MS (EI) 688.3 (MH$^+$).

EXAMPLE 7

N-[2-(4-Cyano-phenyl-ethyl]-2-[5-(3,4-dichloro-benzenesulfonyl)-5,6-dihydro-phenanthridin-6-yl]-acetamide The title compound was prepared from [5-(3,4-dichloro-benzenesulfonyl)-5,6-dihydro-phenanthridin-6-yl]-acetic acid (Example 2c) and 4-(2-amino-ethyl)-benzonitrile [*J. Am. Chem. Soc.* 125 (2003) 7516-7517] according to the method described in Example 1e. MS (EI) 577.2 (MH$^+$).

EXAMPLE 8

N-(4-[1,4']Bipiperidinyl-1-yl-phenyl)-2-[5-(3,4-dichloro-benzenesulfonyl)-5,6-dihydro-phenanthridin-6-yl]-acetamide The title compound was prepared from [5-(3,4-dichloro-benzenesulfonyl)-5,6-dihydro-phenanthridin-6-yl]-acetic acid (Example 2c) and 4-[1,4']bipiperidinyl-1'-yl-phenylamine [*J. Med. Chem.* 46 (2003) 1803-1806] according to the method described in Example 1e. MS (EI) 690.3 (MH+).

EXAMPLE 9

2-[5-(3,4-Dichloro-benzenesulfonyl)-5,6-dihydro-phenanthridin-6-yl]-N-[3-(4-pyridin-4-yl-piperazin-1-yl)-propyl]-acetamide The title compound was prepared from [5-(3,4-dichloro-benzenesulfonyl)-5,6-dihydro-phenanthridin-6-yl]-acetic acid (Example 2c) and 3-(4-pyridin-4-yl-piperazin-1-yl)-propylamine (Reference Example 8) according to the method described in Example 1e. MS (EI) 651.2 (MH+).

EXAMPLE 10

N-(3-[1,4']Bipiperidinyl-1'-yl-propyl)-2-[5-(3,4-dichloro-benzenesulfonyl)-5,6-dihydro-phenanthridin-6-yl]-acetamide The title compound was prepared from [5-(3,4-dichloro-benzenesulfonyl)-5,6-dihydro-phenanthridin-6-yl]-acetic acid (Example 2c) and 3-[1,4']bipiperidinyl-1'-yl)-propylamine trihydrochloride (Reference Example 3) according to the method described in Example 1e. MS (EI) 655.68 (MH+).

EXAMPLE 11

2-[5-(3,4-Dichloro-benzenesulfonyl)-5,6-dihydro-phenanthridin-6-yl]-N-[2-(4-pyridin-2-yl-piperazin-1-yl)-ethyl]-acetamide The title compound was prepared from [5-(3,4-dichloro-benzenesulfonyl)-5,6-dihydro-phenanthridin-6-yl]-acetic acid (Example 2c) and 2-(4-pyridin-2-yl-piperazin-1-yl)-ethylamine tetrahydrochloride (Reference Example 5) according to the method described in Example 1e. MS (EI) 637.3 (MH+).

EXAMPLE 12

2-[5-(3,4-Dichloro-benzenesulfonyl)-5,6-dihydro-phenanthridin-6-yl]-N-{[(piperidin-4-ylmethyl)-carbamoyl]-methyl}-acetamide hydrochloride a) {2-[5-(3,4-Dichloro-benzenesulfoyl)-5,6-dihydro-phenanthridin-6-yl]-acetylamino}-acetic acid methyl ester A solution of [5-(3,4-dichloro-benzenesulfonyl)-5,6-dihydro-phenanthridin-6-yl]-acetic acid (Example 2c) (225 mg, 0.5 mmol), triethylamine (0.14 mL, 1 mmol) and HBTU [O-benzotriazol-1-yl-N,N,N',N'-tetramethyluronium hexafluorophosphate] (208 mg, 0.55 mmol) in dry dimethyl formamide (5 mL) was stirred at room temperature for five minutes before glycin methyl ester hydrochloride (63 mg, 0.5 mmol) was added. The pH of the reaction mixture was adjusted to 8 by addition of triethylamine, the so obtained mixture was stirred at room temperature overnight, then concentrated in vacuo. The residue was purified by preparative thin-layer chromatography (dichlormethane:methanol:NH$_4$OH=15:1:0.1) to yield 248 mg (95%) of the title compound as white crystals.
b) {2-[5-(3,4-Dichloro-benzenesulfonyl)-5,6-dihydroz-phenanthridin-6-yl]-acetylamino}-acetic acid The title compound was prepared from {2-[5-(3,4-dichloro-benzenesulfonyl)-5,6-dihydro-phenanthridin-6-yl]-acetylamino}-acetic acid methyl ester according to the method described in Example 1d.
c) 4-[(2-{2-[5-(3,4-Dichloro-benzenesulfonyl)-5,6-dihydro-phenanthridin-6-yl]-acetylamino}-acetylamino)-methyl]-piperidine-1-carboxylic acid tert-butyl ester The title compound was prepared from {2-[5-(3,4-dichloro-benzenesulfonyl)-5,6-dihydro-phenanthridin-6-yl]-acetylamino}-acetic acid and 4-aminomethyl-piperidine-1-carboxylic acid tert-butyl ester according to the method described in Example 1e.
d) 2-[5-(3,4-Dichloro-benzenesulfonyl)-5,6-dihydro-phenanthridin-6-yl]-N-{[(piperidin-4-ylmethyl)-carbamoyl]-methyl}-acetamide hydrochloride To a solution of 4-[(2-{2-[5-(3,4-dichloro-benzenesulfonyl)-5,6-dihydro-phenanthridin-6-yl]-acetylamino}-acetylamino)-methyl]-piperidine-1-carboxylic acid tert-butyl ester (140 mg, 0.2 mmol) in ethyl acetate (5 mL) 2.4M hydrogen chloride in ethyl acetate (4 mL, 9.6 mmol) was added. The reaction mixture was stirred at room temperature overnight, then diluted with diethyl ether (25 mL). The precipitated product was filtered off and washed with diethyl ether to yield 127 mg (87%) of the title compound as white crystals. MS (EI) 602.2 (MH+).

EXAMPLE 13

2-[5-3,4-Dichloro-benzenesulfonyl)-5,6-dihydro-phenanthridin-6-yl]-N-[(2-piperidin-4-yl-ethylcarbamoyl)-methyl]-acetamide hydrochloride a) 4-[2-(2-{2-[5-(3,4-Dichloro-benzenesulfonyl)-5,6-dihydro-phenanthridin-6-yl]-acetylamino}-acetylamino)-ethyl]-piperidine-1-carboxylic acid tert-butyl ester The title compound was prepared from {2-[5-(3,4-dichloro-benzenesulfonyl)-5,6-dihydro-phenanthridin-6-yl]-acetylamino}-acetic acid (Example 12b) and 4-(2-aminoethyl)-piperidine-1-carboxylic acid tert-butyl ester according to the method described in Example 1e.
b) 2-[5-(3,4-Dichloro-benzenesulfonyl)-5,6-dihydro-phenanthridin-6-yl]-N-[(2-piperidin 4-yl-ethycarbamoyl)-methyl]-acetamide hydrochloride The title compound was prepared from 4-[2-(2-{2-[5-(3,4-dichloro-benzenesulfonyl)-5,6-dihydro-phenanthridin-6-yl]-acetylamino}-acetylamino)-thyl]-piperidine-1-carboxylic acid tert-butyl ester according to the method described in Example 12d. MS (EI) 616.2 (MH+).

EXAMPLE 14

N-{2-[4-(4,5-Dihydro-1H-imidazol-2-yl)-phenyl]-ethyl}-2-[5-(toluene-4-sulfonyl)-5,6-dihydro-phenanthridin-6-yl]-acetamide hydrochloride a) N-Biphenyl-2-yl-4-methyl-benzenesulfonamide The title compound was prepared from 2-aminobiphenyl (Aldrich) and 4-methyl-benzenesulfonyl chloride according to the method described in Example 1b.
b) [5-(Toluene-4-sulfonyl-5,6-dihydro-phenanthridin-6-yl]-acetic acid methyl ester The title compound was prepared from N-biphenyl-2-yl-4-methyl-benzenesulfonamide according to the method described in Example 1c.
c) [5-(Toluene-4-sulfonyl)-5,6-dihydro-phenanthridin-6-yl]-acetic acid The title compound was prepared from [5-(toluene-4-sulfonyl)-5,6-dihydro-phenanthridin-6-yl]-acetic acid methyl ester according to the method described in Example 1d.

d) N-{2-[4-(4,5-Dihydro-1H-imidazol-2-yl)-phenyl]-ethyl}-2-[5-(toluene-4-sulfonyl)-5,6-dihydro-phenanthridin-6-yl]-acetamide hydrochloride The title compound was prepared from [5-(toluene-4-sulfonyl)-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e. MS (EI) 565.7 (MH$^+$).

EXAMPLE 15

N-{2-[4-(4,5-Dihydro-1H-imidazol-2-yl)-phenyl]-ethyl}-2-[5-(2,4,6-trimethyl-benzenesulfonyl)-5,6-dihydro-phenanthridin-6-yl]-acetamide hydrochloride a) N-Biphenyl-2-yl-2,4,4-trimethyl-benzenesulfonamide The title compound was prepared from 2-aminobiphenyl (Aldrich) and 2,4,6-trimethyl-benzenesulfonyl chloride according to the method described in Example 1b.

b) [5-(2,4,6-Trimethyl-benzenesulfonyl)-5,6-dihydro-phenanthridin-6-yl]-acetic acid methyl ester The title compound was prepared from N-biphenyl-2-yl-2,4,6-trimethyl-benzenesulfonamide according to the method described in Example 1c.

c) [5-(2,4,6-Trimethyl-benzenesulfonyl-5,6-dihydro-phenanthridin-6-yl]-acetic acid The title compound was prepared from [5-(2,4,6-trimethyl-benzenesulfonyl)-5,6-dihydro-phenanthridin-6-yl]-acetic acid methyl ester according to the method described in Example 1d.

d) N-{2-[4-(4,5-Dihydro-1H-imidazol-2-yl)-phenyl]-ethyl}-2-[5-(2,4,6-trimethyl-benzenesulfonyl)-5,6-dihydro-phenanthridin-6-yl]-acetamide The title compound was prepared from [5-(2,4,6-trimethyl-benzenesulfonyl)-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e.

EXAMPLE 16

N-{2-[4-(4,5-Dihydro-1H-imidazol-2-yl)-phenyl]-ethyl}-2-[5-(4-methoxy-benzenesulfonyl)-5,6-dihydro-phenanthridin-6-yl]-acetamide hydrochloride a) N-Biphenyl-2-yl-4-methoxy-benzenesulfonamide The title compound was prepared from 2-aminobiphenyl (Aldrich) and 4-methoxy-benzenesulfonyl chloride according to the method described in Example 1b.

b) [5-(4-Methoxy-benzenesulfonyl)-5,6-dihydro-phenanthridin-6-yl]-acetic acid methyl ester The title compound was prepared from N-biphenyl-2-yl-4-methoxy-benzenesulfonamide according to the method described in Example 1c.

c) [5-(4-Methoxy-benzenesulfonyl)-5,6-dihydro-phenanthridin-6-yl]-acetic acid

The title compound was prepared from [5-(4-methoxy-benzenesulfonyl)-5,6-dihydro-phenanthridin-6-yl]-acetic acid methyl ester according to the method described in Example 1d.

d) N-{2-[4-(4,5-Dihydro-1H-imidazol-2-yl)-phenyl]-ethyl}-2-[5-(4-methoxy-benzenesulfonyl)-5,6-dihydro-phenanthridin-6-yl]-acetamide hydrochloride The title compound was prepared from [5-(4-methoxy-benzenesulfonyl)-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e. MS (EI) 581.6 (MH$^+$).

EXAMPLE 17

2-[5-(3,4-Dichloro-benzenesulfonyl)-10-methoxy-5,6-dihydro-phenanthridin-6-yl]-N-{2-[4-(4,5-dihydro-1H-imidazol-2-yl)-phenyl]-ethyl}-acetamide hydrochloride a) 2'-Methoxy-biphenyl-2-ylamine The title compound was prepared from 2-methoxyphenylboronic acid according to the method described in Example 1a.

b) 3,4-Dichloro-N-(2'-methoxy-biphenyl-2-yl)-benzenesulfonamide

The title compound was prepared from 2'-methoxy-biphenyl-2-ylamine according to the method described in Example 1b.

c) [5-(3,4-Dichloro-benzenesulfonyl)-10-methoxy-5,6-dihydro-phenanthridin-6-yl]-acetic acid methyl ester The title compound was prepared from 3,4-dichloro-N-(2'-methoxy-biphenyl-2-yl)-benzenesulfonamide according to the method described in Example 1c.

d) [5-(3,4-Dichloro-benzenesulfonyl)-10-methoxy-5,6-dihydro-phenanthridin-6-yl]-acetic acid The title compound was prepared from [5-(3,4-dichloro-benzenesulfonyl)-10-methoxy-5,6-dihydro-phenanthridin-6-yl]-acetic acid methyl ester according to the method described in Example 1d.

e) 2-[5-(3,4-Dichloro-benzenesulfonyl)-10-methoxy-5,6-dihydro-phenanthridin-6-yl]-N-{2-[4-(4,5-dihydro-1H-imidazol-2-yl)-phenyl]-ethyl}-acetamide hydrochloride The title compound was prepared from [5-(3,4-dichloro-benzenesulfonyl)-10-methoxy-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e.

EXAMPLE 18

2-[5-(3,4-Dichloro-benzenesulfonyl)-8,10-difluoro-5,6-dihydro-phenanthridin-6-yl]-N-{2-[4-(4,5-dihydro-1H-imidazol-2-yl)-phenyl]-ethyl}-acetamide hydrochloride a) 2',4'-Difluoro-biphenyl-2-ylamine The title compound was prepared from 2,4-difluorophenylboronic acid according to the method described in Example 1a.

b) 3,4-Dichloro-N-(2',4,-difluoro-biphenyl-2-yl)-benzenesulfonamide

The title compound was prepared from 2',4'-difluoro-biphenyl-2-ylamine according to the method described in Example 1b.

c) [5-(3,4-Dichloro-benzenesulfonyl)-8,10-difluoro-5,6-dihydro-phenanthridin-6-yl]-acetic acid methyl ester The title compound was prepared from 3,4-dichloro-N-(2',4'-difluoro-biphenyl-2-yl)-benzenesulfonamide according to the method described in Example 1c.

d) [5-(3,4-Dichloro-benzenesulfonyl)-8,10-difluoro-5,6-dihydro-phenanthridin-6-yl]-acetic acid The title compound was prepared from [5-(3,4-dichloro-benzenesulfonyl)-8,10-difluoro-5,6-dihydro-phenanthridin-6-yl]-acetic acid methyl ester according to the method described in Example 1d.

e) 2-[5-(3,4-Dichloro-benzenesulfonyl)-8,10-difluoro-5,6-dihydro-phenanthridin-6-yl]-N-{2-[4-(4,5-dihydro-1H-imidazol-2-yl)-phenyl]-ethyl}-acetamide hydrochloride The title compound was prepared from [5-(3,4-dichloro-benzenesulfonyl)-8,10-difluoro-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e. MS (EI) 656.1 (MH$^+$).

EXAMPLE 19

2-[8-Acetyl-5-(3,4-dichloro-benzenesulfonyl)-5,6-dihydro-phenanthridin-6-yl]-N-{2-[4-(4,5-dihydro-1H-imidazol-2-yl)-phenyl]-ethyl}-acetamide hydrochloride a) 4'-Acetyl-biphenyl-2-ylamine The title compound was prepared from 4-acetylphenylboronic acid according to the method described in Example 1a.

b) N-(4'-Acetyl-biphenyl-2-yl)-3,4-dichloro-benzenesulfonamide

The title compound was prepared from 4'-acetyl-biphenyl-2-ylamine according to the method described in Example 1b.

c) [8-Acetyl-5-(3,4-dichloro-benzenesulfonyl)-5,6-dihydro-phenanthridin-6-yl]-acetic acid methyl ester The title compound was prepared from N-(4'-acetyl-biphenyl-2-yl)-3,4-dichloro-benzenesulfonamide according to the method described in Example 1c.

d) [8-Acetyl-5-(3,4-dichloro-benzenesulfonyl)-5,6-dihydro-phenanthridin-6-yl]-acetic acid The title compound was prepared from [8-acetyl-5-(3,4-dichloro-benzenesulfonyl)-5,6-dihydro-phenanthridin-6-yl]-acetic acid methyl ester according to the method described in Example 1d.

e) 2-[8-Acetyl-5-(3,4-dichloro-benzenesulfonyl)-5,6-dihydro-phenanthridin-6-yl]-N-{2-[4-(4,5-dihydro-1H-imidazol-2-yl)-phenyl]-ethyl}-acetamide hydrochloride The title compound was prepared from [8-acetyl-5-(3,4-dichloro-benzenesulfonyl)-5,6-dihydro-phenanthridin-6-yl]-acetic acid and 2-[4-(4,5-dihydro-1H-imidazol-2-yl)-phenyl]-ethylamine dihydrochloride (Reference Example 2) according to the method described in Example 1e. MS (EI) 662.3 (MH$^+$).

EXAMPLE 20

N-[2-(4-Carbamimidoyl-phenyl)-ethyl]-2-[5-(3,4-dichloro-benzenesulfonyl)-5,6-dihydro-phenanthridin-6-yl]-acetamide A solution of N-[2-(4-cyano-phenyl)-ethyl]-2-[5-(3,4-dichloro-benzenesulfonyl)-5,6-dihydro-phenanthridin-6-yl]-acetamide (Example 7) (200 mg, 0.35 mmol) in 9M hydrogen chloride in ethanol (10 mL) was allowed to stand overnight at room temperature, then the mixture was concentrated in vacuo. The residue was dissolved in ethanol (10 mL) and ammonium carbonate (335 mg, 3.5 mmol) was added. The reaction mixture was stirred overnight at room temperature then concentrated in vacuo. The residue was purified by preparative thin-layer chromatography (dichloromethane:methanol:NH$_4$OH=5:1:0.1) to yield 113 mg (55%) of the title compound as white crystals. MS (EI) 594.1 (MH$^+$).

EXAMPLE 21 trans-2-[5-(3,4-Dichloro-benzenesulfonyl)-10-methoxy-5,6-dihydro-phenanthridine-6-yl]-N-[4-(2-pyrrolidin-1-ylethyl)-cyclohexyl]-acetamide A solution of [5-(3,4-dichloro-benzenesulfonyl)-10-methoxy-5,6-dihydro-phenanthridin-6-yl]-acetic acid (Example 17/d) (0.163 g, 0.34 mmol), triethylamine (0.3 mL, 2.1 mmol) and O-benzotriazol-1-yl-N,N,N',N'-tetramethyluronium hexafluorophosphate (HBTU) (0.152 g, 0.4 mmol) in dry dimethyl formamide (10 mL) was stirred at room temperature for five minutes before trans-4-(2-pyrrolidin-1-yl-ethyl)-cyclohexylamine dihydrochloride (Reference Example 4) (0.09 g, 0.34 mmol) was added. The pH of the reaction mixture was adjusted to 8 by addition of triethylamine, the so obtained mixture was stirred at room temperature overnight, then concentrated in vacuo. The residue was treated with saturated sodium hydrogencarbonate solution (30 mL), the precipitated crystals were filtered off, washed with water and dried. The crude product was purified by column chromatography using Kieselgel 60 (0.040-0.063 mm) (Merck) as adsorbent, and chloroform:methanol:NH$_4$OH=9:1:0.1 as eluent. The product was crystallized with diethyl ether to yield 0.135 g (60%) of the title compound. MS (EI) 657.2 (MH$^+$).

EXAMPLE 22 trans-2-[5-(3,4-Dichloro-benzenesulfonyl)-8,10-dimethoxy-5,6-dihydro-phenanthridin-6-yl]-N-[4-(2-pyrrolidin-1-ylethyl)-cyclohexyl]-acetamide a) 2',4'-Dimethoxy-biphenyl-2-ylamine The title compound was prepared from 2,4-dimethoxyphenylboronic acid according to the method described in Example 1a.

b) 3,4-Dichloro-N-(2',4'-dimethoxy-biphenyl-2-yl)-benzenesulfonamide

The title compound was prepared from 2',4'-dimethoxy-biphenyl-2-ylamine according to the method described in Example 1b.

c) [5-(3,4-Dichloro-benzenesulfonyl-8,10-dimethoxy-5,6-dihydro-phenanthridin-6-yl]-acetic acid methyl ester The title compound was prepared from 3,4-dichloro-N-(2',4'-dimethoxy-biphenyl-2-yl)-benzenesulfonamide according to the method described in Example 1c.

d) [5-(3,4-Dichloro-benzenesulfonyl)-8,10-dimethoxy-5,6-dihydro-phenanthridin-6-yl]-acetic acid The title compound was prepared from [5-(3,4-dichloro-benzenesulfonyl)-8,10-dimethoxy-5,6-dihydro-phenanthridin-6-yl]-acetic acid methyl ester according to the method described in Example 1d.

e) 2-[5-(3,4-Dichloro-benzenesulfonyl)-8,10-dimethoxy-5,6-dihydro-phenanthridin-6-yl]-N-{2-[4-(4,5-dihydro-1H-imidazol-2-yl)-phenyl]-ethyl}-acetamide hydrochloride The title compound was prepared from [5-(3,4-dichloro-benzenesulfonyl)-8,10-dimethoxy-5,6-dihydro-phenanthridin-6-yl]-acetic acid and trans-4-(2-pyrrolidin-1-yl-ethyl)-cyclohexylamine dihydrochloride (Reference Example 4) according to the method described in Example 21. MS (EI) 687.2 (MH$^+$).

EXAMPLE 23

Preparation of Pharmaceutical Compositions a) Tablets:

0.01-50% of active ingredient of formula (I), 15-50% of lactose, 15-50% of potato starch, 5-15% of polyvinyl pyrrolidone, 1-5% of talc, 0.01-3% of magnesium stearate, 1-3% of colloid silicon dioxide and 2-7% of ultraamylopectin were mixed, then granulated by wet granulation and pressed to tablets.

b) Dragées, Film Coated Tablets:

The tablets made according to the method described above were coated by a layer consisting of entero- or gastrosolvent film, or of sugar and talc. The dragées were polished by a mixture of beeswax and carnuba wax.

c) Capsules:

0.01-50% of active ingredient of formula (I), 1-5% of sodium lauryl sulfate, 15-50% of starch, 15-50% of lactose, 1-3% of colloid silicon dioxide and 0.01-3% of magnesium stearate were thoroughly mixed, the mixture was passed through a sieve and filled in hard gelatin capsules.

d) Suspensions:

Ingredients: 0.01-15% of active ingredient of formula (I), 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrilic acid), 0.1-5% of 96% ethanol, 0.1-1% of flavoring agent, 20-70% of sorbitol (70% aqueous solution) and 30-50% of distilled water.

To solution of nipagin and citric acid in 20 ml of distilled water, carbopol was added in small portions under vigorous stirring, and the solution was left to stand for 10-12 h. Then the sodium hydroxide in 1 ml of distilled water, the aqueous solution of sorbitol and finally the ethanolic raspberry flavor were added with stirring. To this carrier the active ingredient was added in small portions and suspended with an immersing homogenizator. Finally the suspension was filled up to the desired final volume with distilled water and the suspension syrup was passed through a colloid milling equipment.

e) Suppositories:

For each suppository 0.01-15% of active ingredient of formula (I) and 1-20% of lactose were thoroughly mixed, then 50-95% of adeps pro suppository (for example Witepsol 4) was melted, cooled to 35° C. and the mixture of active ingredient and lactose was mixed in it with homogenizator. The obtained mixture was mould in cooled forms.

f) Lyophilized Powder Ampoule Compositions.

A 5% solution of mannitol or lactose was made with bidistilled water for injection use, and the solution was filtered so as to have sterile solution. A 0.01-5% solution of the active ingredient of formula (I) was also made with bidistilled water for injection use, and this solution was filtered so as to have sterile solution. These two solutions were mixed under aseptic conditions, filled in 1 ml portions into ampoules, the content of the ampoules was lyophilized, and the ampoules were sealed under nitrogen. The contents of the ampoules were dissolved in sterile water or 0.9% (physiological) sterile aqueous sodium chloride solution before administration.

The invention claimed is:

1. A new bradykinin B1 receptor antagonist phenanthridine compound of formula (I):

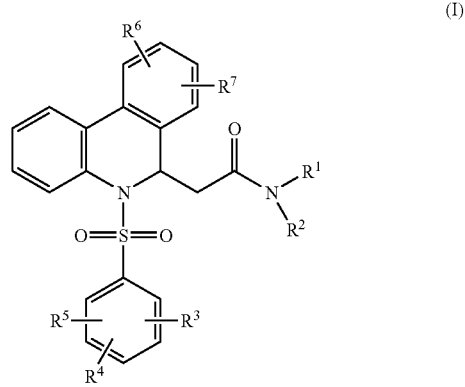

wherein $R_1$ is hydrogen or C1-C4 alkyl;

$R_2$ is selected from (1) hydrogen atom; with the proviso that $R_1$ and $R_2$ can not be simultaneously hydrogen atom; (2) —$(CH_2)_n$—$NR^aR^b$, (3) —$(CH_2)_n$CO—$NR^aR^b$, (4) —$(CH_2)_m$—X-Q, and (5) —$CHR^c$—$NR^aR^b$; or $R_1$ and $R_2$ together with the nitrogen atom to which they are attached form a 4-7 membered heterocyclic ring containing 1-3 heteroatom(s) selected from O, S and N; wherein said ring is optionally substituted with —CO—$NR^aR^b$, $C_1$-$C_4$ alkyl, 4-(4,5-dihydro-1H-imidazol-2-yl)-benzyl or 4-(1,4,5,6-tetrahydro-pyrimidin-2-yl)-benzyl;

$R^3$, $R^4$, $R^5$, $R^6$ and $R^7$ are independently selected from hydrogen, halogen, trifluoromethyl, $C_1$-$C_4$ alkyl, $C_1$-$C_4$ alkoxy, and acetyl;

n is an integer from 1 to 4;

$R^a$ and $R^b$ are hydrogen atom, optionally substituted $C_1$-$C_4$ alkyl group, or $R^a$, $R^b$ and the nitrogen atom to which they are both attached together form a saturated, partially unsaturated or aromatic 4-7 membered ring containing 1-3 heteroatom(s) selected from 0, S and N; wherein said ring is optionally substituted with 1-piperidinyl, 2-piperidinyl, 4-piperidinyl, 2-pyridyl or 4-pyridyl group;

$R^c$ is methyl, hydroxymethyl, benzyl or phenyl group;

m is an integer from 0 to 6;

X is a single bond, O or S; and,

Q is a phenyl group, optionally substituted with [1,4']bipiperidinyl-1'-yl, 4,5-dihydro-1H-imidazol-2-yl, —$(CH_2)_n$NH—(C=NH)—$NH_2$, or —$(CH_2)_m$(C=NH)—$NH_2$; or a 4-piperidinyl group, optionally substituted with a 4-piperidinyl group; or a $C_5$-$C_7$ cycloalkyl group, optionally substituted with a —$(CH_2)_m$—$NR^aR^b$ group;

and optical antipodes, racemates, or salts thereof.

2. The compound of formula (I) of claim 1 selected from the group consisting of:

2-[5-(3,4-dichloro-benzenesulfonyl)-8-fluoro-5,6-dihydro-phenanthridin-6-yl]-N-{2-[4-(4,5-dihydro-1H-imidazol-2-yl)-phenyl]-ethyl}-acetamide hydrochloride, 2-[5-(3,4-dichloro-benzenesulfonyl)-5,6-dihydro-phenanthridin-6-yl]-N-{2-[4-(4,5-dihydro-1H-imidazol-2-yl)-phenyl]-ethyl}-acetamide hydrochloride, 2-[5-(3,4-dichloro-benzenesulfonyl)-5,6-dihydro-phenanthridin-6-yl]N[2-(4-pyridin-4-yl-piperazin-1-yl)-ethyl]-acetamide, trans-2-[5-(3,4-dichloro-benzenesulfonyl)-5,6-dihydro-phenanthridin-6-yl]-N-[4-(2-pyrrolidin-1-yl-ethyl)-cyclohexyl]-acetamide, 2-[5-(3,4-dichloro-benzenesulfonyl)-5,6-dihydro-phenanthridin-6-yl]-1-{4-[4-(4,5-dihydro-1H-imidazol-2-yl)-benzyl]-piperidin-1-yl}-ethanone, 2-[5-(3,4-dichloro-benzenesulfonyl)-5,6-dihydro-phenanthridin-6-yl]-1-{4-[4-(1,4,5,6-tetrahydro-pyrimidin-2-yl)-benzyl]-piperidin-1-yl}-ethanone, N-(4-[1,4']bipiperidinyl-1'-yl-phenyl)-2-[5-(3,4-dichloro-benzenesulfonyl)-5,6-dihydro-phenanthridin-6-yl]-acetamide, 2-[5-(3,4-dichloro-benzenesulfonyl)-5,6-dihydro-phenanthridin-6-yl]-N-[3-(4-pyridin-4-yl-piperazin-1-yl)-propyl]-acetamide, N-{2-[4-(4,5-dihydro-1H-imidazol-2-yl)-phenyl]-ethyl}-2-[5-(toluene-4-sulfonyl)-5,6-dihydro-phenanthridin-6-yl]-acetamide hydrochloride, N-{2-[4-(4,5-dihydro-1H-imidazol-2-yl)-phenyl]-ethyl}-2-[5-(2,4,6-trimethyl-benzenesulfonyl)-5,6-dihydro-phenanthridin-6-yl]-acetamide hydrochloride, N-{2-[4-(4,5-dihydro-1H-imidazol-2-yl)-phenyl]-ethyl}-2-[5-(4-methoxy-benzenesulfonyl)-5,6-dihydro-phenanthridin-6-yl]-acetamide hydrochloride, 2-[5-(3,4-dichloro-benzenesulfonyl)-10-methoxy-5,6-dihydro-phenanthridin-6-yl]-N-{2-[4-(4,5-dihydro-1H-imidazol-2-yl)-phenyl]-ethyl}-acetamide hydrochloride, 2-[5-(3,4-dichloro-benzenesulfonyl)-8,10-difluoro-5,6-dihydro-phenanthridin-6-yl]-N-{2-[4-(4,5-dihydro-1H-imidazol-2-yl)-phenyl]-ethyl}-acetamide hydrochloride, 2-[8-acetyl-5-(3,4-dichloro-benzenesulfonyl)-5,6-dihydro-phenanthridin-6-yl]-N-{2-[4-(4,5-dihydro-1H-imidazol-2-yl)-phenyl]-ethyl}-acetamide hydrochloride, N-[2-(4-carbamimidoyl-phenyl)-ethyl]-2-[5-(3,4-dichloro-benzenesulfonyl)-5,6-dihydro-phenanthridin-6-yl]-acetamide; and trans-2-[5-(3,4-dichloro-benzenesulfonyl)-10-methoxy-5,6-dihydro-phenanthridine-6-yl]-N-[4-(2-pyrrolidin-1-ylethyl)-cyclohexyl]-acetamide.

3. A process for preparing the compounds of formula (I) as claimed in claim 1, comprising reacting a boronic acid derivative of formula (II):

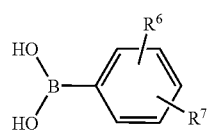
(II)

wherein R6 and R7 are independently selected from hydrogen, halogen, trifluoromethyl, C1-C4 alkyl, C1-C4 alkoxy, and acetyl, with 2-bromoaniline of formula (III)

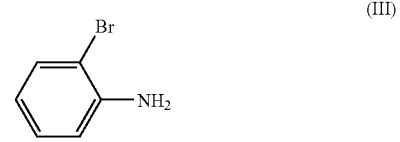
(III)

in the presence of a catalyst to obtain an amino-biphenyl derivative of formula (IV):

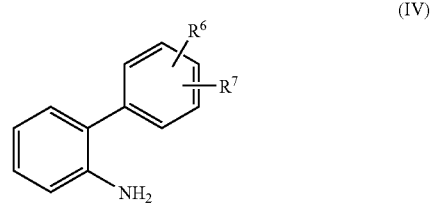
(IV)

wherein $R^6$ and $R^7$ are as defined above;

thereafter the amino-biphenyl derivative of formula (IV) is sulfonylated with a sulfochloride derivative of formula (V):

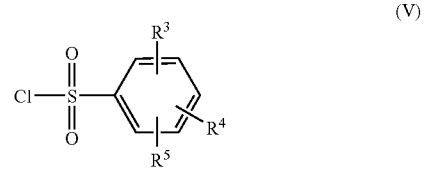
(V)

wherein R3, R4, and R5, are also independently selected from hydrogen, halogen, trifluoromethyl, C1-C4 alkyl, C1-C4 alkoxy, and acetyl to form a sulfonamide derivative of formula (VI)

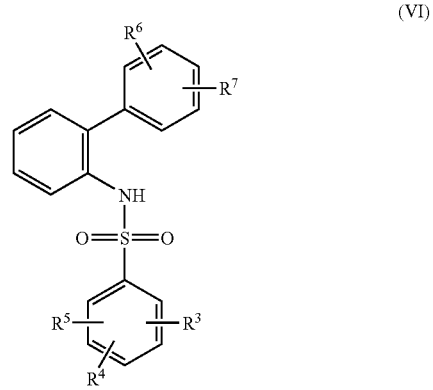
(VI)

wherein $R^3$, $R^4$, $R^5$, $R^6$ and $R^7$ are as defined above;

thereafter the sulfonamide derivative of formula (VI) is submitted to cyclization reaction to obtain a phenathridine acetic acid ester derivative of formula (VII):

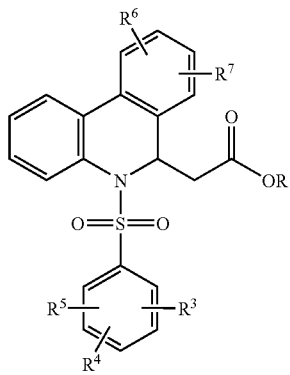

(VII)

wherein the meaning of $R^3$, $R^4$, $R^5$, $R^6$ and $R^7$ are as defined above and R is $C_1$-$C_4$ alkyl group;

hydrolyzing the phenathridine acetic acid ester derivative of formula (VII) in the presence of a base to furnish a phenathridine acetic acid derivative of formula (VIII)

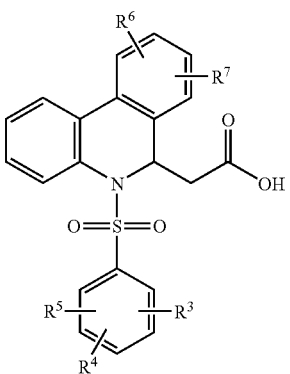

(VIII)

wherein the meaning of $R^3$, $R^4$, $R^5$, $R^6$ and $R^7$ are as defined above; and reacting the phenathridine acetic acid derivative of formula (VIII) with an amine derivative of formula (IX)

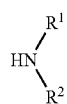

(IX)

wherein
R1 is hydrogen or C1-C4 alkyl;
R2 is selected from (1) hydrogen atom; with the proviso that R1 and R2 can not be simultaneously hydrogen atom; (2) —(CH2)n-$NR^aR^b$, (3) —(CH2)n CO—$NR^aR^b$, (4) —(CH2)m X-Q, and (5) —$CHR^c$—$NR^aR^b$; or
R1 and R2 together with the nitrogen atom to which they are attached form a 4-7 membered heterocyclic ring containing 1-3 heteroatom(s) selected from O, S and N; wherein said ring is optionally substituted with —CO—$NR^aR^b$, C1-C4 alkyl, 4-(4,5-dihydro-1H-imidazol-2-yl)-benzyl or 4-(1,4,5,6-tetrahydro-pyrimidin-2-yl)-benzyl;

n is an integer from 1 to 4;
$R^a$ and $R^b$ are hydrogen atom, optionally substituted C1-C4 alkyl group, or $R^a$, $R^b$ and the nitrogen atom to which they are both attached together form a saturated, partially unsaturated or aromatic 4-7 membered ring containing 1-3 heteroatom(s) selected from 0, S and N; wherein said ring is optionally substituted with 1-piperidinyl, 2-piperidinyl, 4-piperidinyl, 2-pyridyl or 4-pyridyl group;

$R^c$ is methyl, hydroxymethyl, benzyl or phenyl group;
m is an integer from 0 to 6;
X is a single bond, O or S; and,
Q is a phenyl group, optionally substituted with [1,4']bipiperidinyl-1'-yl, 4,5-dihydro-1H -imidazol-2-yl, —(CH2)n NH—(C=NH)—NH2, or —(CH$_2$)m (C=NH)—NH2; or a 4-piperidinyl group, optionally substituted with a 4-piperidinyl group; or a C5-C7 cycloalkyl group, optionally substituted with a —(CH2) m-$NR^aR^b$ group.

4. The process of claim 3, wherein the catalyst is tetrakis (triphenylphosphine)-palladium(0).

5. A process for preparing the compounds of formula (I) as claimed in claim 1, comprising: transforming a compound of formula (I) into another compound of formula (I) by at least one of: introducing new substituents, modifying existing substituents, removing existing substituents, forming a salt, or liberating a compound from a salt.

6. A compound of formula (IX):

(IX)

wherein R1 is hydrogen or C1-C4 alkyl;
R2 is selected from (1) hydrogen atom; with the proviso that R1 and R2 can not be simultaneously hydrogen atom; (2) —(CH2)n-$NR^aR^b$, (3) —(CH2)n CO—$NR^aR^b$, (4) —(CH2)m —X-Q, and (5) —$CHR^c$—$NR^aR^b$; or
R1 and R2 together with the nitrogen atom to which they are attached form a 4-7 membered heterocyclic ring containing 1-3 heteroatom(s) selected from O, S and N; wherein said ring is optionally substituted with —CO—$NR^aR^b$, C1-C4 alkyl, 4-(4,5-dihydro-1H-imidazol-2-yl)-benzyl or 4-(1,4,5,6-tetrahydro-pyrimidin-2-yl)-benzyl;
wherein the compound of formula (IX) is selected from: 2-(4-pyridin-4-yl -piperazin-1-yl)-ethylamine, trans-4-(2-pyrrolidin-1-yl-ethyl)-cyclohexylamine dihydrochloride, 2-(4-pyridin-2-yl-piperazin-1-yl)-ethylamine tetrahydrochloride, 4-[4-(4,5-dihydro-1H-imidazol-2-yl)-benzyl]-piperidine, 2-(4-piperidin-4-ylmethyl-phenyl)-1,4,5,6-tetrahydro -pyrimidine, and 2-(4-pyridin-4-yl-piperazin-1-yl)-propylamine.

7. A pharmaceutical composition comprising a therapeutically effective amount of a compound of formula (I) as claimed in claim 1 or optical antipodes or racemates or pharmaceutically acceptable salts thereof; and one or more pharmaceutically acceptable excipients.

* * * * *

UNITED STATES PATENT AND TRADEMARK OFFICE
CERTIFICATE OF CORRECTION

PATENT NO. : 8,034,827 B2
APPLICATION NO. : 12/158606
DATED : October 11, 2011
INVENTOR(S) : Gyula Beke It is certified that error appears in the above-identified patent and that said Letters Patent is hereby corrected as shown below:

Title Page, Item [73] Assignee, delete "Gegeon" and insert --Gedeon-- therefor;

Title Page, Foreign Application Priority Data, delete "0501169" and insert --P0501169-- therefor;

Title Page, References Cited, Other Publications, Bergbreiter reference, delete "dyes,"*Org.*" and insert --dyes," *Org.*-- therefor;

Column 1, line 9, Cross-Reference to Related Applications, delete "PCT/HU20006/000120" and insert --PCT/HU2006/000120-- therefor;

Column 28, line 23 (Claim 1), delete "$R_1$" and insert --$R^1$-- therefor;

Column 28, line 23 (Claim 1), delete "C1-C4" and insert --$C_1$-$C_4$-- therefor;

Column 28, line 24 (Claim 1), delete "$R_2$" and insert --$R^2$-- therefor;

Column 28, line 29 (Claim 1), delete "$R_1$ and $R_2$" and insert --$R^1$ and $R^2$-- therefor;

Column 28, line 45 (Claim 1), delete "0" and insert --O-- therefor;

Column 28, line 53 (Claim 1), delete "4,5-dihydro-1H   -imidazol-2-yl," and insert --4,5-dihydro-1H-imidazol-2-yl,-- therefor;

Column 29, line 2 (Claim 2), delete "phenanthridin-6-yl]N[2-(4-pyridi-4-yl-piperazin-1-" and insert --phenanthridin-6-yl]-N-[2-(4-pyridi-4-yl-piperazin-1- -- therefor;

Column 29, line 51 (Claim 3), delete "compounds" and insert --compound-- therefor;

Column 29, line 53 (Claim 3), delete "(II )" and insert --(II)-- therefor;

Signed and Sealed this
Twenty-ninth Day of November, 2011

David J. Kappos
*Director of the United States Patent and Trademark Office*

CERTIFICATE OF CORRECTION (continued)
U.S. Pat. No. 8,034,827 B2

Column 30, line 1 (Claim 3), delete "R6 and R7" and insert --$R^6$ and $R^7$-- therefor;

Column 30, line 2 (Claim 3), delete "C1-C4 alkyl, C1-C4" and insert --$C_1$-$C_4$ alkyl, $C_1$-$C_4$-- therefor;

Column 30, line 44 (Claim 3), delete "R3, R4, and R5," and insert --$R^3$, $R^4$, and $R^5$,-- therefor;

Column 30, line 45 (Claim 3), delete "C1-C4" and insert --$C_1$-$C_4$-- therefor;

Column 30, line 46 (Claim 3), delete "C1-C4" and insert --$C_1$-$C_4$-- therefor;

Column 31, lines 2-3 (Claim 3), delete "phenathridine" and insert --phenanthridine-- therefor;

Column 31, line 24 (Claim 3), delete "phenathridine" and insert --phenanthridine-- therefor;

Column 31, line 26 (Claim 3), delete "phenathridine" and insert --phenanthridine-- therefor;

Column 31, line 47 (Claim 3), delete "phenathridine" and insert --phenanthridine-- therefor;

Column 31, line 58 (Claim 3), delete "R1 is hydrogen or C1-C4" and insert --$R^1$ is hydrogen or $C_1$-$C_4$-- therefor;

Column 31, line 59 (Claim 3), delete "R2" and insert --$R^2$-- therefor;

Column 31, line 60 (Claim 3), delete "R1 and R2" and insert --$R^1$ and $R^2$-- therefor;

Column 31, line 61 (Claim 3), delete "(CH2)n-$NR^aR^b$,(3)-(CH2)n" and insert --$(CH_2)_n$-$NR^aR^b$,(3)-$(CH_2)_n$-- therefor;

Column 31, line 62 (Claim 3), delete "(CH2)m" and insert --$(CH_2)_m$-- therefor;

Column 31, line 64 (Claim 3), delete "R1 and R2" and insert --$R^1$ and $R^2$-- therefor;

Column 32, line 1 (Claim 3), delete "C1-C4" and insert --$C_1$-$C_4$-- therefor;

Column 32, line 5 (Claim 3), delete "C1-C4" and insert --$C_1$-$C_4$-- therefor;

Column 32, line 9 (Claim 3), delete "0" and insert --O-- therefor;

Column 32, line 18 (Claim 3), delete "(CH2)nNH-(C=NH)–NH2, or –(CH2)m" and insert --$(CH_2)_n$NH-(C=NH)–$NH_2$, or –$(CH_2)_m$-- therefor;

Column 32, line 19 (Claim 3), delete "NH2" and insert --$NH_2$-- therefor;

Column 32, line 20 (Claim 3), delete "C5-C7" and insert --$C_5$-$C_7$-- therefor;

CERTIFICATE OF CORRECTION (continued)
U.S. Pat. No. 8,034,827 B2

Column 32, line 21 (Claim 3), delete "(CH2)" and insert --(CH$_2$)-- therefor;

Column 32, line 40 (Claim 6), delete "R1 is hydrogen or C1-C4" and insert --R$^1$ is hydrogen or C$_1$-C$_4$-- therefor;

Column 32, line 41 (Claim 6), delete "R2" and insert --R$^2$-- therefor;

Column 32, line 42 (Claim 6), delete "R1 and R2" and insert --R$^1$ and R$^2$-- therefor;

Column 32, line 43 (Claim 6), delete "(CH2)n-NR$^a$R$^b$,(3)—(CH2)n" and insert --(CH$_2$)$_n$-NR$^a$R$^b$,(3) –(CH$_2$)$_n$-- therefor;

Column 32, line 44 (Claim 6), delete "(CH2)m" and insert --(CH$_2$)$m$-- therefor;

Column 32, line 46 (Claim 6), delete "R1 and R2" and insert --R$^1$ and R$^2$-- therefor;

Column 32, line 50 (Claim 6), delete "C1-C4" and insert --C$_1$-C$_4$-- therefor;

Column 32, line 54 (Claim 6), delete "4-yl -piperazin" and insert --4-yl-piperazin-- therefor;

Column 32, line 59 (Claim 6), delete "6-tetrahydro -pyrimidine," and insert --6-tetrahydro-pyrimidine,-- therefor.